US011197810B2

(12) United States Patent
Hertenstein et al.

(10) Patent No.: US 11,197,810 B2
(45) Date of Patent: Dec. 14, 2021

(54) HAIR CARE COMPOSITIONS COMPRISING MALODOR REDUCTION COMPOSITIONS

(71) Applicant: The Procter & Gamble Company, Cincinnati, OH (US)

(72) Inventors: Stacy Renee Hertenstein, Mason, OH (US); Judith Ann Hollingshead, Batavia, OH (US); Jennifer Anne Corder, West Chester Township, OH (US); James Anthony Staudigel, Loveland, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/810,222

(22) Filed: Mar. 5, 2020

(65) Prior Publication Data

US 2020/0197272 A1  Jun. 25, 2020

Related U.S. Application Data

(62) Division of application No. 15/467,331, filed on Mar. 23, 2017, now Pat. No. 10,610,473.

(60) Provisional application No. 62/312,856, filed on Mar. 24, 2016.

(51) Int. Cl.
| | | |
|---|---|---|
| *A61K 8/33* | (2006.01) | |
| *A61K 8/23* | (2006.01) | |
| *A61K 8/31* | (2006.01) | |
| *A61K 8/34* | (2006.01) | |
| *A61K 8/35* | (2006.01) | |
| *A61K 8/37* | (2006.01) | |
| *A61K 8/49* | (2006.01) | |
| *A61Q 5/00* | (2006.01) | |
| *A61Q 5/02* | (2006.01) | |
| *A61Q 5/12* | (2006.01) | |

(52) U.S. Cl.
CPC .................. *A61K 8/33* (2013.01); *A61K 8/23* (2013.01); *A61K 8/31* (2013.01); *A61K 8/34* (2013.01); *A61K 8/35* (2013.01); *A61K 8/37* (2013.01); *A61K 8/498* (2013.01); *A61K 8/4973* (2013.01); *A61Q 5/002* (2013.01); *A61Q 5/006* (2013.01); *A61Q 5/02* (2013.01); *A61Q 5/12* (2013.01); *A61K 2800/77* (2013.01)

(58) Field of Classification Search
None
See application file for complete search history.

(56) References Cited

U.S. PATENT DOCUMENTS

| | | |
|---|---|---|
| 1,489,388 A | 4/1924 | Glenn |
| 1,600,340 A | 9/1926 | Hoffman |
| 1,612,255 A | 12/1926 | Borreca |
| 2,438,091 A | 3/1948 | Lynch |
| 2,528,378 A | 10/1950 | Mannheimer |
| 2,658,072 A | 11/1953 | Kosmin |
| 2,809,971 A | 10/1957 | Bernstein |
| 3,236,733 A | 2/1966 | Karsten |
| 3,373,208 A * | 3/1968 | Blumenthal ............ C07C 43/18 568/665 |
| 3,636,113 A | 1/1972 | Hall |
| 3,716,498 A | 2/1973 | Hall |
| 3,753,196 A | 8/1973 | Kurtz et al. |
| 3,761,418 A | 9/1973 | Parran |
| 3,792,068 A | 2/1974 | Luedders |
| 3,887,692 A | 6/1975 | Gilman |
| 3,904,741 A | 9/1975 | Jones et al. |
| 4,049,792 A | 9/1977 | Elsnau |
| 4,089,945 A | 5/1978 | Brinkman et al. |
| 4,120,948 A | 10/1978 | Shelton |
| 4,137,180 A | 1/1979 | Naik et al. |
| 4,237,155 A | 12/1980 | Kardouche |
| 4,323,683 A | 4/1982 | Bolich, Jr. et al. |
| 4,345,080 A | 8/1982 | Bolich, Jr. |
| 4,359,456 A | 11/1982 | Gosling et al. |
| 4,379,753 A | 4/1983 | Bolich, Jr. |
| 4,430,243 A | 2/1984 | Bragg |
| 4,470,982 A | 9/1984 | Winkler |
| 4,854,333 A | 8/1989 | Inman et al. |
| 4,931,274 A | 6/1990 | Barabino et al. |
| 4,973,416 A | 11/1990 | Kennedy |
| 4,985,238 A | 1/1991 | Tanner et al. |

(Continued)

FOREIGN PATENT DOCUMENTS

| | | |
|---|---|---|
| BE | 825146 A1 | 8/1975 |
| BR | 199400875 A | 10/1995 |

(Continued)

OTHER PUBLICATIONS

14034 PCT International Search Report and Written Opinion, dated Jan. 12, 2016 (13 pages), International Application No. PCT/US2015/052092.

Air Quality of the Iowa Department of Natural Resources. A Review of the Science and Technology of Odor Measurement, 2005, 51 pages (2005).

All final and non-final office actions for U.S. Appl. No. 14/864,927 (P&G Case 13564M), (filing date Sep. 25, 2015).

All final and non-final office actions for U.S. Appl. No. 14/864,973 (P&G Case 14031), (filing date Sep. 25, 2015).

All final and non-final office actions for U.S. Appl. No. 14/864,994 (P&G Case 14032), (filing date Sep. 25, 2015).

(Continued)

*Primary Examiner* — Bethany P Barham
*Assistant Examiner* — Barbara S Frazier
(74) *Attorney, Agent, or Firm* — Linda M. Sivik

(57) ABSTRACT

The present invention relates to hair care compositions comprising malodor reduction compositions and methods of using such hair care compositions. Such hair care compositions comprising the malodor control technologies disclosed herein provide malodor control without leaving an undesirable scent and when perfume is used to scent such compositions, such scent is not unduly altered by the malodor control technology.

6 Claims, No Drawings

(56) References Cited

U.S. PATENT DOCUMENTS

| | | | |
|---|---|---|---|
| 5,019,375 A | 5/1991 | Tanner et al. | |
| 5,104,646 A | 4/1992 | Bolich, Jr. et al. | |
| 5,106,609 A | 4/1992 | Bolich, Jr. et al. | |
| 5,135,747 A | 8/1992 | Faryniarz | |
| 5,296,622 A | 3/1994 | Uphues et al. | |
| 5,429,816 A | 7/1995 | Hofrichter et al. | |
| 5,486,303 A | 1/1996 | Capeci et al. | |
| 5,489,392 A | 2/1996 | Capeci et al. | |
| 5,516,448 A | 5/1996 | Capeci et al. | |
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,595,967 A | 1/1997 | Miracle et al. | |
| 5,597,936 A | 1/1997 | Perkins et al. | |
| 5,624,666 A | 4/1997 | Coffindaffer | |
| 5,665,267 A | 9/1997 | Dowell et al. | |
| 5,691,297 A | 11/1997 | Nassano et al. | |
| 5,714,137 A | 2/1998 | Trinh et al. | |
| 5,800,897 A | 9/1998 | Sharma | |
| 5,879,584 A | 3/1999 | Bianchetti et al. | |
| 5,891,424 A | 4/1999 | Bretzler et al. | |
| 5,942,217 A | 8/1999 | Woo et al. | |
| 5,976,514 A | 11/1999 | Guskey et al. | |
| 6,153,567 A | 11/2000 | Hughes | |
| 6,180,121 B1 | 1/2001 | Guenin et al. | |
| 6,225,464 B1 | 5/2001 | Hiler, II et al. | |
| 6,232,302 B1 | 5/2001 | Alberico et al. | |
| 6,248,135 B1 | 6/2001 | Trinh et al. | |
| 6,352,688 B1 | 3/2002 | Scavone et al. | |
| 6,386,392 B1 | 5/2002 | Argentieri et al. | |
| 6,413,920 B1 | 7/2002 | Bettiol et al. | |
| 6,436,442 B1 | 8/2002 | Woo et al. | |
| 6,488,943 B1 | 12/2002 | Beerse et al. | |
| 6,649,155 B1 | 11/2003 | Dunlop et al. | |
| 6,656,923 B1 | 12/2003 | Trinh et al. | |
| 6,660,288 B1 | 12/2003 | Behan | |
| 6,679,324 B2 | 1/2004 | Den Boer et al. | |
| 6,716,805 B1 | 4/2004 | Sherry et al. | |
| 6,740,713 B1 | 5/2004 | Busch | |
| 6,764,986 B1 | 7/2004 | Busch | |
| 6,767,507 B1 | 7/2004 | Woo | |
| 6,794,356 B2 | 9/2004 | Turner | |
| 6,814,088 B2 | 11/2004 | Barnabas et al. | |
| 6,869,923 B1 | 3/2005 | Cunningham et al. | |
| 6,908,889 B2 | 6/2005 | Niemiec et al. | |
| 7,018,978 B2 | 3/2006 | Miracle et al. | |
| 7,100,767 B2 | 9/2006 | Chomik | |
| 7,151,079 B2 | 12/2006 | Fack et al. | |
| 7,172,099 B2 | 2/2007 | Hofte et al. | |
| 7,202,198 B2 | 4/2007 | Gordon et al. | |
| 7,223,361 B2 | 5/2007 | Kvietok et al. | |
| 7,841,036 B2 | 11/2010 | Smith | |
| 7,867,505 B2 | 1/2011 | Elliott et al. | |
| 8,007,545 B2 | 8/2011 | Fujii | |
| 8,058,500 B2 | 11/2011 | Sojka | |
| 8,158,571 B2 | 4/2012 | Alonso | |
| 8,322,631 B2 | 12/2012 | Richardson et al. | |
| 8,357,359 B2 | 1/2013 | Woo et al. | |
| 8,539,631 B2 | 9/2013 | Catalfamo | |
| 8,574,561 B1 | 11/2013 | Patel et al. | |
| 8,609,600 B2 | 12/2013 | Warr et al. | |
| 8,679,316 B2 | 3/2014 | Brunner et al. | |
| 8,709,337 B2 | 4/2014 | Gruenbacher et al. | |
| 8,741,275 B2 | 6/2014 | Dente | |
| 8,772,354 B2 | 7/2014 | Williams et al. | |
| 8,931,711 B2 | 1/2015 | Gruenbacher et al. | |
| 8,987,187 B2 | 3/2015 | Smets et al. | |
| 9,949,911 B2 | 4/2018 | Cetti | |
| 10,039,706 B2 | 8/2018 | Meralli et al. | |
| 10,113,140 B2 | 10/2018 | Frankenbach | |
| 10,182,976 B2 | 1/2019 | Staudigel | |
| 10,238,685 B2 | 3/2019 | Dunn et al. | |
| 10,392,625 B2 | 8/2019 | Jin et al. | |
| 10,610,473 B2 | 4/2020 | Hertenstein et al. | |
| 2002/0012646 A1 | 1/2002 | Royce et al. | |
| 2002/0172648 A1 | 11/2002 | Hehner et al. | |
| 2003/0003070 A1 | 1/2003 | Eggers et al. | |
| 2003/0008787 A1 | 1/2003 | Mcgee et al. | |
| 2003/0192922 A1 | 10/2003 | Ceppaluni | |
| 2004/0064117 A1 | 4/2004 | Hammons et al. | |
| 2004/0151793 A1 | 8/2004 | Paspaleeva-kuhn et al. | |
| 2005/0003975 A1 | 1/2005 | Browne et al. | |
| 2005/0003980 A1 | 1/2005 | Baker et al. | |
| 2005/0192207 A1 | 9/2005 | Morgan, III | |
| 2005/0245407 A1 | 11/2005 | Ishihara et al. | |
| 2005/0276831 A1 | 12/2005 | Dihora et al. | |
| 2006/0005333 A1 | 1/2006 | Catalfamo | |
| 2006/0009337 A1 | 1/2006 | Smith | |
| 2006/0084589 A1 | 4/2006 | Vlad et al. | |
| 2006/0166857 A1 | 7/2006 | Surburg | |
| 2006/0171911 A1 | 8/2006 | Schwartz et al. | |
| 2007/0003499 A1 | 1/2007 | Shen et al. | |
| 2007/0020263 A1 | 1/2007 | Shitara et al. | |
| 2007/0275866 A1 | 11/2007 | Dykstra | |
| 2007/0298994 A1 | 12/2007 | Finke | |
| 2008/0003245 A1 | 1/2008 | Kroepke et al. | |
| 2008/0176780 A1 | 7/2008 | Warr | |
| 2008/0194454 A1 | 8/2008 | Morgan | |
| 2009/0005280 A1 | 1/2009 | Woo | |
| 2009/0240223 A1 | 9/2009 | Warren et al. | |
| 2009/0312223 A1 | 12/2009 | Yang | |
| 2010/0000116 A1 | 1/2010 | Aouad | |
| 2010/0001116 A1 | 1/2010 | Johnson | |
| 2010/0009285 A1 | 1/2010 | Daems et al. | |
| 2010/0061946 A1 | 3/2010 | Scherner et al. | |
| 2010/0087357 A1 | 4/2010 | Morgan, III et al. | |
| 2010/0152083 A1 | 6/2010 | Velazquez | |
| 2010/0168251 A1* | 7/2010 | Warr | A61K 8/498 514/772 |
| 2010/0215775 A1 | 8/2010 | Schmaus et al. | |
| 2010/0287710 A1 | 11/2010 | Denutte et al. | |
| 2010/0322878 A1 | 12/2010 | Stella et al. | |
| 2011/0098209 A1 | 4/2011 | Smets et al. | |
| 2011/0107524 A1 | 5/2011 | Chieffi et al. | |
| 2011/0118691 A1 | 5/2011 | Nishitani | |
| 2011/0245134 A1 | 10/2011 | Smets et al. | |
| 2011/0245136 A1 | 10/2011 | Smets et al. | |
| 2011/0269657 A1 | 11/2011 | Dihora | |
| 2011/0303766 A1 | 12/2011 | Smith | |
| 2011/0305778 A1 | 12/2011 | Caggioni et al. | |
| 2011/0308555 A1 | 12/2011 | Smets | |
| 2011/0308556 A1 | 12/2011 | Smets et al. | |
| 2012/0004328 A1 | 1/2012 | Huchel et al. | |
| 2012/0009285 A1 | 1/2012 | Wei et al. | |
| 2012/0129924 A1 | 5/2012 | Park et al. | |
| 2012/0219610 A1 | 8/2012 | Smith, III et al. | |
| 2012/0230936 A1 | 9/2012 | Mikkelsen | |
| 2012/0237469 A1 | 9/2012 | Dente | |
| 2012/0246851 A1 | 10/2012 | Smith, III et al. | |
| 2012/0258150 A1 | 10/2012 | Rauckhorst et al. | |
| 2013/0043145 A1 | 2/2013 | Smith, III et al. | |
| 2013/0043146 A1 | 2/2013 | Smith, III et al. | |
| 2013/0043147 A1 | 2/2013 | Smith, III et al. | |
| 2013/0136713 A1 | 5/2013 | Terada | |
| 2013/0266642 A1 | 10/2013 | Hollingshead | |
| 2013/0319463 A1 | 12/2013 | Policicchio | |
| 2014/0186864 A1 | 7/2014 | Kato et al. | |
| 2014/0201927 A1 | 7/2014 | Bianchetti et al. | |
| 2014/0221269 A1 | 8/2014 | Sobel et al. | |
| 2015/0108163 A1 | 4/2015 | Smith et al. | |
| 2015/0141310 A1 | 5/2015 | Smets et al. | |
| 2015/0231045 A1 | 8/2015 | Krohn et al. | |
| 2015/0352027 A1 | 12/2015 | Thomas et al. | |
| 2016/0089317 A1 | 3/2016 | Cetti et al. | |
| 2016/0089318 A1 | 3/2016 | Cetti et al. | |
| 2016/0089462 A1 | 3/2016 | Frankenbach et al. | |
| 2016/0089464 A1 | 3/2016 | Frankenbach et al. | |
| 2016/0089465 A1 | 3/2016 | Frankenbach et al. | |
| 2016/0090555 A1 | 3/2016 | Frankenbach et al. | |
| 2016/0090556 A1 | 3/2016 | Frankenbach et al. | |
| 2016/0090557 A1 | 3/2016 | Frankenbach et al. | |
| 2016/0090558 A1 | 3/2016 | Frankenbach et al. | |
| 2016/0092661 A1 | 3/2016 | Hollingshead et al. | |

(56) References Cited

U.S. PATENT DOCUMENTS

| | | |
|---|---|---|
| 2016/0206522 A1 | 7/2016 | Ribaut |
| 2016/0250115 A1 | 9/2016 | Li et al. |
| 2016/0296656 A1 | 10/2016 | Scavone et al. |
| 2016/0306909 A1 | 10/2016 | Hollingshead et al. |
| 2016/0317424 A1 | 11/2016 | Kadir et al. |
| 2016/0326458 A1 | 11/2016 | Smets et al. |
| 2017/0066579 A1 | 3/2017 | Voigt et al. |
| 2017/0119917 A1 | 5/2017 | Frankenbach et al. |
| 2017/0137752 A1 | 5/2017 | Frankenbach et al. |
| 2017/0137753 A1 | 5/2017 | Frankenbach et al. |
| 2017/0249407 A1 | 8/2017 | Cetti et al. |
| 2017/0249408 A1 | 8/2017 | Cetti et al. |
| 2017/0252273 A1 | 9/2017 | Renock et al. |
| 2017/0255725 A1 | 9/2017 | Frankenbach et al. |
| 2017/0333591 A9 | 11/2017 | Scavone |
| 2017/0367963 A1 | 12/2017 | Kadir et al. |
| 2018/0004875 A1 | 1/2018 | Cetti et al. |
| 2018/0066210 A1 | 3/2018 | Frankenbach et al. |
| 2018/0311135 A1 | 11/2018 | Chang et al. |
| 2019/0155975 A9 | 5/2019 | Cetti |
| 2020/0206110 A1 | 7/2020 | Hertenstein et al. |
| 2021/0169765 A1 | 6/2021 | Renock |

FOREIGN PATENT DOCUMENTS

| | | | |
|---|---|---|---|
| CA | 704195 A | 2/1965 | |
| CA | 1164347 A | 3/1984 | |
| CA | 1248458 A | 1/1989 | |
| CN | 1823929 A | 8/2006 | |
| CN | 100534415 C | 9/2009 | |
| CN | 101112349 B | 5/2011 | |
| CN | 101690697 B | 10/2011 | |
| CN | 101559034 B | 1/2013 | |
| CN | 102973437 A | 3/2013 | |
| CN | 104107401 A | 10/2014 | |
| CN | 107595657 A | 1/2018 | |
| CN | 107595673 A | 1/2018 | |
| CN | 107737329 A | 2/2018 | |
| DE | 2145204 A1 | 3/1973 | |
| DE | 3018456 A1 | 11/1981 | |
| DE | 102004012009 A1 | 9/2005 | |
| DE | 102004023720 A1 | 12/2005 | |
| DE | 102007019369 A1 | 10/2008 | |
| DE | 102014225083 A1 | 10/2015 | |
| DE | 102014225606 A1 | 10/2015 | |
| EP | 0108517 A2 | 5/1984 | |
| EP | 0666358 A1 | 8/1995 | |
| EP | 0545556 B1 | 7/1997 | |
| EP | 2005939 A1 | 12/2008 | |
| EP | 1970045 A3 | 9/2009 | |
| ES | 2052450 B1 | 12/1994 | |
| FR | 2669531 A1 | 5/1992 | |
| FR | 2795955 A1 | 1/2001 | |
| GB | 190110699 A | 8/1901 | |
| GB | 191023922 A | 10/1911 | |
| GB | 2048229 | 12/1980 | |
| GB | 1347950 | 3/1985 | |
| GB | 2144992 | 3/1985 | |
| GB | 2450727 | 1/2009 | |
| HU | 42318 T | 12/1985 | |
| JP | S58198412 A | 11/1983 | |
| JP | AS60004598 A | 1/1985 | |
| JP | S62205200 A | 9/1987 | |
| JP | S63165308 A | 7/1988 | |
| JP | H06220495 A | 8/1994 | |
| JP | H10017894 A | 1/1998 | |
| JP | 2000178586 A | 6/2000 | |
| JP | 2001011492 A | 1/2001 | |
| JP | 2001011497 A | 1/2001 | |
| JP | 2001254099 A | 9/2001 | |
| JP | 2001261529 A | 9/2001 | |
| JP | 2002336337 A | 11/2002 | |
| JP | 2003082398 A | 3/2003 | |
| JP | 2003171688 A | 6/2003 | |
| JP | 2003176497 A | 6/2003 | |
| JP | 2003261413 A | 9/2003 | |
| JP | 2003268398 A | 9/2003 | |
| JP | 2003342131 A | 12/2003 | |
| JP | 2006063044 A | 3/2006 | |
| JP | 2006104149 A | 4/2006 | |
| JP | 2006249092 A | 9/2006 | |
| JP | 2007177047 A | 7/2007 | |
| JP | 2007223935 A | 9/2007 | |
| JP | 2011241353 A | 12/2011 | |
| JP | 2014502519 A | 2/2014 | |
| JP | 2014516054 A | 7/2014 | |
| KR | 100290589 B1 | 9/2001 | |
| KR | 100821846 B1 | 4/2008 | |
| KR | 20090095359 A | 9/2009 | |
| KR | 20100040180 A | 4/2010 | |
| KR | 101494008 B1 | 2/2015 | |
| KR | 101503922 B1 | 3/2015 | |
| KR | 101532070 B1 | 7/2015 | |
| UA | 50333 U | 5/2010 | |
| WO | WO-8603679 A1 * | 7/1986 | ............. A61P 17/00 |
| WO | 9502389 A2 | 1/1995 | |
| WO | WO9604937 A1 | 2/1996 | |
| WO | WO9604940 A1 | 2/1996 | |
| WO | WO9957233 A1 | 11/1999 | |
| WO | WO0032601 | 6/2000 | |
| WO | WO02064722 A2 | 8/2002 | |
| WO | 03096998 A1 | 11/2003 | |
| WO | 2008017540 A1 | 2/2008 | |
| WO | 2012055812 A1 | 5/2012 | |
| WO | 2012127009 A1 | 9/2012 | |
| WO | WO2012136651 A1 | 10/2012 | |
| WO | WO2013018805 A1 | 2/2013 | |
| WO | 2014111667 A2 | 7/2014 | |
| WO | 2014111668 A2 | 7/2014 | |
| WO | 2015085376 A1 | 6/2015 | |
| WO | 2018109148 A1 | 6/2018 | |

OTHER PUBLICATIONS

All final and non-final office actions for U.S. Appl. No. 14/865,010 (P&G Case 14033), (filing date Sep. 25, 2015).
All final and non-final office actions for U.S. Appl. No. 14/865,048 (P&G Case 14034), (filing date Sep. 25, 2015).
All final and non-final office actions for U.S. Appl. No. 14/865,056 (P&G Case 14028), (filing date Sep. 25, 2015).
All final and non-final office actions for U.S. Appl. No. 14/865,066 (P&G Case 14036), (filing date Sep. 25, 2015).
All final and non-final office actions for U.S. Appl. No. 14/865,089 (P&G Case 14037), (filing date Sep. 25, 2015).
All final and non-final office actions for U.S. Appl. No. 14/865,099 (P&G Case 14038), (filing date Sep. 25, 2015).
All final and non-final office actions for U.S. Appl. No. 14/865,257 (P&G Case 14035), (filing date Sep. 25, 2015).
All final and non-final office actions for U.S. Appl. No. 14/865,4126 (P&G Case 14039), (filing date Sep. 25, 2015).
All final and non-final office actions for U.S. Appl. No. 15/196,081 (P&G Case 14031C), (filing date Sep. 25, 2015).
All final and non-final office actions for U.S. Appl. No. 15/407,477 (P&G Case 13564MC), (filing date Sep. 25, 2015).
All final and non-final office actions for U.S. Appl. No. 15/421,481 (P&G Case 14033C), (filing date Sep. 25, 2015).
All final and non-final office actions for U.S. Appl. No. 15/421,642 (P&G Case 14039C), (filing date Sep. 25, 2015).
All final and non-final office actions for U.S. Appl. No. 15/432,957 (P&G Case 14038C), (filing date Sep. 25, 2015).
All final and non-final office actions for U.S. Appl. No. 15/467,331 (P&G Case 14270M), (filing date Sep. 25, 2015).
All final and non-final office actions for U.S. Appl. No. 15/597,048 (P&G Case 14034D), (filing date Sep. 25, 2015).
All final and non-final office actions for U.S. Appl. No. 15/597,391 (P&G Case 14035D), (filing date Sep. 25, 2015).
All final and non-final office actions for U.S. Appl. No. 15/708,205 (P&G Case 14035D2), (filing date Sep. 25, 2015).
All final and non-final office actions for U.S. Appl. No. 15/716,544 (P&G Case 14039CC), (filing date Sep. 25, 2015).

(56) References Cited

OTHER PUBLICATIONS

ASTM D3954-94, Reapproved 2010, vol. 15.04, Standard Test Method for Dropping Point of Waxes.

ASTM-Designation: D3954-94 (Reapproved 2010); Standard Test Method for Dropping Point of Waxes; Downloaded Wed. Aug. 19, 2015; 2 pages.

Brattoli et al. Odour Detection Methods: Olfactometry and Chemical Sensors. Sensors (Basel), 2011; 11(5); 5290-5322(2011).

Chemical Book (Chemical Book, Isolongifolone, available at http://www.chemicalbook.com/ProductChemicalPropertiesCB5318980_EN.htm), (2016).

Crepaldi, E.L., et al., Chemical, Structural, and Thermal Properties of Zn(II)—Cr(III) Layered Double Hydroxides Intercalated with Sulfated and Sulfonated Surfactants, Journal of Colloid and Interface Science, 2002, pp. 429-442, vol. 248.

Database WPI; Week 201459; Thomson scientific, London, GB; AN 2014-P66521; XP002752638, (2014).

International Search Report; International Application No. PCT/US2015/052219; dated Jan. 26, 2016; 13 pages.

McGinley et al. American Association of Textile Chemists and Colorists, 2017, 17 pages, (2017).

McGinley et al. Performance Verification of Air Freshener Products and Other Odour Control Devices for Indoor Air Quality Malodours. Presented at the 8th Workshop on Odour and Emissions of Plastic Materials Universitat Kassel Institut for Wesrkstofftechnik Kassel, Germany, Mar. 27-28, 2006, 13 pages.

Morioka, H. et al. "Effects of Zinc on the New Preparation Method of Hydroxy Double Salts" Inorg. Chem. 1999, 38, 4211-6.

PCT International Search Report and Written Opinion for PCT/US2015/052084 dated Jan. 19, 2016.

PCT International Search Report and Written Opinion for PCT/US2015/052088 dated Jan. 22, 2016.

PCT International Search Report and Written Opinion for PCT/US2015/052089 dated Feb. 23, 2016.

PCT International Search Report and Written Opinion for PCT/US2015/052090 dated Jan. 19, 2016.

PCT International Search Report and Written Opinion for PCT/US2015/052092 dated Jan. 12, 2016.

PCT International Search Report and Written Opinion for PCT/US2015/052093 dated Jan. 12, 2016.

PCT International Search Report and Written Opinion for PCT/US2015/052094 dated Jan. 20, 2016.

PCT International Search Report and Written Opinion for PCT/US2015/052119 dated Jan. 20, 2016.

PCT International Search Report and Written Opinion for PCT/US2015/052130 dated Jan. 12, 2016.

PCT International Search Report and Written Opinion for PCT/US2015/052219 dated Jan. 26, 2016.

PCT International Search Report and Written Opinion for PCT/US2015/052225 dated Jan. 20, 2016.

PCT International Search Report and Written Opinion for PCT/US2017/023758 dated May 23, 2017, (incomplete).

Todd et al., Volatile Silicone Fluids for Cosmetics, Cosmetics and Toiletries, vol. 91, pp. 27-32 (Jan. 1976).

Database GNPD [Online] MINTEL;Mar. 28, 2018 (Mar. 28, 2018),anonymous: Dandruff Control Shampoo 11 , XP055787038,Database accession No. 5556267abstract, 3 Pgs.

Database GNPD [Online] MINTEL;Apr. 5, 2005 (Apr. 5, 2005),anonymous: "Anticaspa-Graso Anti-DandruffShampoo",XPC:I55787029,Database accession No. 351776paragraph [ingredients], 2 pgs . . . .

Grillet et al. , "Polymer Gel Rheology and Adhesion", Rheology, 2012, pp. 59-80.

Sensory.,"A Review of The Science and Technology of Odor Measurement", Prepared for the Air Quality Bureau of the Iowa Department of Natural Resources, Dec. 30, 2005 51 pages.

Pending U.S. Appl. No. 17/111,906, filed Dec. 4, 2020, to Eric Scott Johnson et al.

All Office Actions; U.S. Appl. No. 16/810,207, filed Mar. 4, 2020.

\* cited by examiner

HAIR CARE COMPOSITIONS COMPRISING MALODOR REDUCTION COMPOSITIONS

FIELD OF THE INVENTION

The present invention relates to hair care compositions comprising malodor reduction compositions and methods of making and using such hair care compositions.

BACKGROUND OF THE INVENTION

Unscented or lightly scented products are desired by consumers as they may be considered more natural and discreet than more highly scented products. Manufacturers of unscented or lightly scented products for controlling malodors rely on malodor reduction ingredients or other technologies (e.g. filters) to reduce malodors. However, effectively controlling malodors, for example, amine-based malodors (e.g. fish and urine), thiol and sulfide-based malodors (e.g. garlic and onion), $C_2$-$C_{12}$ carboxylic acid based malodors (e.g. body and pet odor), indole based malodors (e.g. fecal and bad breath), short chain fatty aldehyde based malodors (e.g. grease) and geosmin based malodors (e.g. mold/mildew) may be difficult, and the time required for a product to noticeably reduce malodors may create consumer doubt as to the product's efficacy on malodors. Often times, manufacturers incorporate scented perfumes to help mask these difficult malodors.

Unfortunately, malodor control technologies typically cover up the malodor with a stronger scent and thus interfere with the scent of the perfumed or unperfumed situs that is treated with the malodor control technology. Thus, limited nature of the current malodor control technologies is extremely constraining. Thus what is needed is a broader palette of malodor control technologies so the perfume community can deliver the desired level of character in a greater number of situations/applications. Surprisingly, Applicants recognized that in addition to blocking a malodor's access to a sensory cell, in order to achieve the desired goal, a malodor control technology must leave such sensor cell open to other molecules, for example scent molecules. Thus, hair care compositions comprising the malodor control technologies disclosed herein provide malodor control without leaving an undesirable scent and, when perfume is used to scent such compositions, such scent is not unduly altered by the malodor control technology.

Selenium sulfide containing anti-fungal hair and scalp care compositions provide some of the most effective protection from and relief of dandruff conditions. Historically, selenium sulfide and other sulfur-based formulations are highly medicinal and pungent smelling—both in use and throughout the day—due to residual sulfur compounds deposited on the hair and scalp. These significant negative cosmetic attributes may cause consumers to avoid selenium sulfide and other sulfur-based formulations and therefore product usage compliance is difficult and as a result consumers often do not find complete relief from their dandruff condition.

SUMMARY OF THE INVENTION

The present invention relates a hair care composition comprising, based on total composition weight: a sum total of from about 0.0001% to about 2% of alpha,alpha,6,6-tetramethylbicyclo[3.1.1]hept-2-ene-propanal) and one or more malodor reduction materials having a Sulfur MORV>3; from about 0.01% to about 10% of a scalp active material selected from the group consisting of selenium sulfide, sulfur and mixtures thereof; from about 0.1% to about 40%, of a surfactant.

DETAILED DESCRIPTION OF THE INVENTION

Definitions

"Hair Care" composition" as defined herein, may include shampoos, conditioners and leave-on-treatments.

"Rinse-off" means the intended product usage includes application to hair followed by rinsing and/or wiping the product from the skin and/or hair within a few seconds to minutes of the application step.

"STnS" refers to sodium trideceth(n) sulfate, wherein n can define the average number of moles of ethoxylate per molecule.

As used herein "MORV" is the calculated malodor reduction value for a subject material. A material's MORV indicates such material's ability to decrease or even eliminate the perception of one or more malodors. For purposes of the present application, a material's MORV is calculated in accordance with method found in the test methods section of the present application.

As used herein, "malodor" refers to compounds generally offensive or unpleasant to most people, such as the complex odors associated with bowel movements.

As used herein, "odor blocking" refers to the ability of a compound to reduce the perception of a malodor.

As used herein, the term "perfume" does not include malodor reduction materials. Thus, the perfume portion of a composition does not include, when determining the perfume's composition, any malodor reduction materials found in the composition as such malodor reduction materials are described herein. In short, if a material has a malodor reduction value "MORV" that is within the range of the MORV recited in the subject claim, such material is a malodor reduction material for purposes of such claim.

As used herein, the terms "a" and "an" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Hair Care Compositions

Rinse-off hair care compositions can come in a variety of forms. For example, a hair care composition can be in a liquid form and can be a shampoo, conditioning shampoo, Hair Care compositions can include perfume materials. Many consumers prefer hair care compositions that can consistently provide a desired scent, or odor that can be perceived each time the product is used. Perfume materials can provide the desired scent or odor to these hair care compositions. These perfume (i.e., fragrance) materials can include perfumes, perfume raw materials, and perfume delivery systems.

Malodor Reduction Materials

A non-limiting set of suitable malodor reduction materials are provided in the tables below.

TABLE 1

List of materials with Sulfur MORV > 3

| Number | CAS Number | Name | ACD Room Temp (25 C.) Vapor Pressure (mm Hg, ACD, EXP-14-AA6010-003) | Octanol/Water Partition Coefficient, logP (ACD, Consensus algorithm, EXP-14-AA6010-002) | Malodor Reduction: Log (1/EC0) 3-methyl-3-sulfanylhexan-1-ol (3M3S1H) |
|---|---|---|---|---|---|
| | 188199-50-0 | 2'-isopropyl-1,7,7-trimethylspiro[bicyclo[2.2.1]heptane-2,4'-[1,3]dioxane] | 2.3E−02 | 4.30 | 3.04 |
| | 154171-77-4 | (1',1',5',5'-tetramethylhexahydro-2'H,5'H-spiro[[1,3]dioxolane-2,8'-[2,4a]methanonaphthalene] K | 1.5E−02 | 4.51 | 4.66 |
| | 5413-60-5 | 3a,4,5,6,7,7a-hexahydro-1H-4,7-methanoinden-6-yl acetate) | 1.4E−02 | 2.79 | 3.44 |
| | 68480-11-5 | Decahydro-3H-spiro[furan-2,5'-[4,7]methanoindene] | 1.4E−02 | 3.36 | 3.22 |
| | 19870-74-7 | CEDRYL METHYL ETHER | 1.3E−02 | 5.08 | 5.52 |
| | 116126-82-0 | Ethyl (1R,2R,3R,4R)-3-isopropylbicyclo[2.2.1]hept-5-ene-2-carboxylate | 1.2E−02 | 3.68 | 3.22 |
| | 3738-00-9 | 3aR,5aR,9aR,9bR)-3a,6,6,9a-tetramethyldodecahydronaphtho[2,1-b]furan | 9.3E−03 | 5.11 | 3.06 |
| | 33885-52-8 | alpha,alpha,6,6-tetramethyl bicyclo[3.1.1]hept-2-ene-propanal | 6.9E−03 | 4.31 | 3.18 |
| | 1139-30-6 | 4,5-epoxy-4,11,11-trimethyl-8-methylenebicyclo(7.2.0)undecane) | 6.7E−03 | 4.47 | 3.57 |
| | 41724-19-0 | 4aR,8aS)-7-methyloctahydro-1,4-methanonaphthalen-6(2H)-one | 6.5E−03 | 2.66 | 3.43 |
| | 86803-90-9 | 5-methoxyoctahydro-1H-4,7-methanoindene-2-carbaldehyde | 4.4E−03 | 2.08 | 3.87 |
| | 68738-96-5 | 8,8-dimethyl-6,7-dihydro-5H-naphthalene-2-carbaldehyde | 4.4E−03 | 3.92 | 3.11 |
| | 41816-03-9 | 2R,4a'R,8a'R)-3,7'-dimethyl-3',4',4a',5',8',8a'-hexahydro-1'H-spiro[oxirane-2,2'-[1,4]methanonaphthalene]) | 3.3E−03 | 3.09 | 3.57 |
| | 476332-65-7 | (2,2,6,6,7,8,8-heptamethyldecahydro-2H-indeno[4,5-b]furan | 3.2E−03 | 6.14 | 5.66 |
| | 23787-90-8 | 1,3,4,6,7,8alpha-hexahydro-1,1,5,5-tetramethyl-2H-2,4alpha-methanophtalen-8(5H)-one) | 2.6E−03 | 4.09 | 4.53 |
| | 67634-20-2 | 3a,4,5,6,7,7a-hexahydro-1H-4,7-methanoinden-5-yl isobutyrate | 2.4E−03 | 3.51 | 4.13 |
| | 57345-19-4 | 3S,5aR,7aS,11aS,11bR)-3,8,8,11a-tetramethyldodecahydro-5H-3,5a-epoxynaphtho[2,1-c]oxepine | 2.0E−03 | 5.18 | 4.97 |
| | 68912-13-0 | (8,8-dimethyl-3a,4,5,6,7,7a-hexahydro-1H-4,7-methanoinden-6-yl propionate) | 1.8E−03 | 4.00 | 5.04 |
| | 211299-54-6 | 4aR,5R,7aS,9R)-2,2,5,8,8,9a-hexamethyloctahydro-4H-4a,9-methanoazuleno[5,6-d][1,3]dioxole | 1.8E−03 | 4.85 | 6.82 |
| | 68901-32-6 | 2-(8-isopropyl-6-methylbicyclo[2.2.2]oct-5-en-2-yl)-1,3-dioxolane | 1.2E−03 | 3.81 | 3.04 |
| | 68039-44-1 | 3a,4,5,6,7,7a-hexahydro-1H-4,7-methanoinden-6-yl pivalate | 1.2E−03 | 3.96 | 3.79 |
| | 823178-41-2 | 3a,5,6,7,8,8b-hexahydro-2,2,6,6,7,8,8-heptamethyl-4H-indeno(4,5-d)-1,3-dioxole | 7.4E−04 | 4.97 | 5.24 |

TABLE 1-continued

List of materials with Sulfur MORV > 3

| Number | CAS Number | Name | ACD Room Temp (25 C.) Vapor Pressure (mm Hg, ACD, EXP-14-AA6010-003) | Octanol/Water Partition Coefficient, logP (ACD, Consensus algorithm, EXP-14-AA6010-002) | Malodor Reduction: Log (1/EC0) 3-methyl-3-sulfanylhexan-1-ol (3M3S1H) |
|---|---|---|---|---|---|
| | 39900-38-4 | (3R-(3alpha,3a,6alpha,7,8aalpha))-octahydro-3,6,8,8-tetramethyl-1H-3a,7-methanoazulen-6-yl formate | 6.3E−04 | 4.97 | 4.83 |
| | 77-53-2 | (1S,2R,5S,7R,8R)-2,6,6,8-tetramethyltricyclo[5.3.1.01,5]undecan-8-ol | 5.7E−04 | 4.49 | 4.40 |
| | 54464-57-2 | 1-((2S,3S)-2,3,8,8-tetramethyl-1,2,3,4,5,6,7,8-octahydronaphthalen-2-yl)ethan-1-one | 5.4E−04 | 4.72 | 3.26 |
| | 30168-23-1 | ((E)-4-((3aS,7aS)-octahydro-5H-4,7-methanoinden-5-ylidene)butanal | 4.4E−04 | 3.97 | 4.42 |
| | 5986-55-0 | 1R-(1alpha,4beta,4aalpha,6beta,8aalpha))-octahydro-4,8a,9,9-tetramethyl-1,6-methano-1(2H)-naphthol | 2.8E−04 | 4.46 | 4.34 |
| | 32214-91-8 | [(3Z)-4,11,11-trimethyl-8-methylidene-5-bicyclo[7.2.0]undec-3-enyl] acetate | 2.5E−04 | 5.50 | 3.55 |
| | 552-02-3 | (1aR,4S,4aS,7R,7aS,7bS)-1,1,4,7-tetramethyldecahydro-1H-cyclopropa[e]azulen-4-ol | 1.8E−04 | 4.72 | 4.12 |
| | 69486-14-2 | Z)-6-ethylideneoctahydro-2H-5,8-methanochromen-2-one) | 1.1E−04 | 2.32 | 3.82 |
| | 32388-55-9 | 1-((3R,3aR,7R,8aS)-3,6,8,8-tetramethyl-2,3,4,7,8,8a-hexahydro-1H-3a,7-methanoazulen-5-yl)ethan-1-one | 8.5E−05 | 4.97 | 4.49 |
| | 167254-80-0 | 3,5,5,6,7,8,8-heptamethyl-5,6,7,8-tetrahydronaphthalene-2-carbonitrile | 6.9E−05 | 5.88 | 3.36 |
| | 66072-32-0 | 4-(1,7,7-trimethyl-6-bicyclo[2.2.1]heptanyl)cyclohexan-1-ol | 3.0E−05 | 4.45 | 3.50 |
| | 501929-47-1 | (E)-4-((3aR,4R,7R,7aR)-1,3a,4,6,7,7a-hexahydro-5H-4,7-methanoinden-5-ylidene)-3-methylbutan-2-ol | 8.5E−06 | 3.87 | 5.44 |
| | 3681-73-0 | (E)-3,7-dimethylocta-2,6-dien-1-yl palmitate) | 3.0E−09 | 10.75 | 3.31 |

TABLE 2

List of materials with Sulfur MORV > 3; ClogP > 3 and VP > .005

| Number | Material Name | CAS Number | ACD Room Temp (25 C.) Vapor Pressure (mm Hg, ACD, EXP-14-AA6010-003) | Octanol/Water Partition Coefficient, logP (ACD, Consensus algorithm, EXP-14-AA6010-002) | Malodor Reduction: Log (1/EC0) 3-methyl-3-sulfanylhexan-1-ol (3M3S1H) |
|---|---|---|---|---|---|
| 1 | 2'-isopropyl-1,7,7-trimethylspiro[bicyclo[2.2.1]heptane-2,4'-[1,3]dioxane | 188199-50-0 | 2.3E−02 | 4.30 | 3.04 |
| 2 | (1',1',5',5'-tetramethylhexahydro-2'H,5'H-spiro[[1,3]dioxolane-2,8'-[2,4a]methanonaphthalene] K | 154171-77-4 | 1.5E−02 | 4.51 | 4.66 |
| 3 | SPIRO[FURAN-2(3H),5'-(4,7-METHANO-5H-INDENE], DECAHYDRO | 68480-11-5 | 1.4E−02 | 3.36 | 3.22 |

TABLE 2-continued

List of materials with Sulfur MORV > 3; ClogP > 3 and VP > .005

| Number | Material Name | CAS Number | ACD Room Temp (25 C.) Vapor Pressure (mm Hg, ACD, EXP-14-AA6010-003) | Octanol/Water Partition Coefficient, logP (ACD, Consensus algorithm, EXP-14-AA6010-002) | Malodor Reduction: Log (1/EC0) 3-methyl-3-sulfanylhexan-1-ol (3M3S1H) |
|---|---|---|---|---|---|
| 4 | (3R,3aR,6S,7S,8aS)-6-methoxy-3,6,8,8-tetramethyloctahydro-1H-3a,7-methanoazulene | 19870-74-7 | 1.3E−02 | 5.08 | 5.52 |
| 5 | Ethyl (1R,2R,3R,4R)-3-isopropylbicyclo[2.2.1]hept-5-ene-2-carboxylate | 116126-82-0 | 1.2E−02 | 3.68 | 3.22 |
| 6 | 3aR,5aR,9aR,9bR)-3a,6,6,9a-tetramethyldodecahydronaphtho[2,1-b]furan | 3738-00-9 | 9.3E−03 | 5.11 | 3.06 |
| 7 | (alpha,alpha,6,6-tetramethyl bicyclo[3.1.1]hept-2-ene-propanal) | 33885-52-8 | 6.9E−03 | 4.31 | 3.18 |
| 8 | 4,5-epoxy-4,11,11-trimethyl-8-methylenebicyclo(7.2.0)undecane) | 1139-30-6 | 6.7E−03 | 4.47 | 3.57 |
| 9 | 2'-isopropyl-1,7,7-trimethylspiro[bicyclo[2.2.1]heptane-2,4'-[1,3]dioxane | 188199-50-0 | 2.3E−02 | 4.30 | 3.04 |

TABLE 3

Sulfor MORV > 3 and ClogP > 3

| 11 | 1,3,4,6,7,8alpha-hexahydro-1,1,5,5-tetramethyl-2H-2,4alpha-methanophtalen-8(5H)-one) | 23787-90-8 | 2.6E−03 | 4.09 | 4.53 |
|---|---|---|---|---|---|
| 12 | 8,8-dimethyl-3a,4,5,6,7,7a-hexahydro-1H-4,7-methanoinden-6-yl propionate) | 68912-13-0 | 1.8E−03 | 4.00 | 5.04 |
| 13 | 2-(8-isopropyl-6-methylbicyclo[2.2.2]oct-5-en-2-yl)-1,3-dioxolane | 68901-32-6 | 1.2E−03 | 3.81 | 3.04 |
| 14 | [(3Z)-4,11,11-trimethyl-8-methylidene-5-bicyclo[7.2.0]undec-3-enyl] acetate | 32214-91-8 | 2.5E−04 | 5.50 | 3.55 |
|  | (E)-3,7-dimethylocta-2,6-dien-1-yl palmitate) | 3681-73-0 | 3.0E−09 | 10.75 | 3.31 |

The materials in Tables 1-3 may be supplied by one or more, but not limited to, the following: Firmenich Inc. of Plainsboro N.J. USA; International Flavor and Fragrance Inc. New York, N.Y. USA; Takasago Corp. Teterboro, N.J. USA; Symrise Inc. Teterboro, N.J. USA; Sigma-Aldrich/SAFC Inc. Carlsbad, Calif. USA; and Bedoukian Research Inc. Danbury, Conn. USA.

In one aspect of said hair care composition, said composition comprises one or more perfume raw materials.

In one aspect of said hair care composition, said composition comprises a total of, based on total consumer product weight, from about 0.1% to about 7% of one or more of said malodor reduction materials and from about 3% to about 30% of a surfactant, and, optionally, a miscellar phase and/or lamellar phase.

In one aspect of said hair care composition, said composition comprises a total, based on total consumer product weight, of from about 0.1% to about 50% of a material selected from structurants, humectants, fatty acids, inorganic salts, antimicrobial agents, antimicrobial agents actives and mixtures thereof.

In one aspect of said hair care composition, said composition comprises an adjunct ingredient selected from the group consisting of clay mineral powders, pearl pigments, organic powders, emulsifiers, distributing agents, pharmaceutical active, topical active, preservatives, surfactants and mixtures thereof.

A method of controlling malodors comprising: contacting a situs comprising a malodor and/or a situs that will become malodorous with a hair care composition selected from the group consisting of the hair care compositions disclosed herein is disclosed.

In one aspect of said method, said situs comprises the head of hair and said contacting step comprises contacting said hair containing a malodor with a sufficient amount of present invention's hair care composition to provide said hair with a level of malodor reduction material at least 0.0001 mg of malodor reduction material per body or head of hair, in an embodiment from about 0.0001 mg of malodor reduction material per head of hair to about 1 mg of malodor reduction material per head of hair, in a further embodiment from about 0.001 mg of malodor reduction material per head of hair about 0.5 mg of malodor reduction material per body or head of hair, a further embodiment from about 0.01 of malodor reduction material per head of hair to about 0.2 mg of malodor reduction material per head of hair.

Adjunct Materials

While not essential for the purposes of the present invention, the non-limiting list of adjuncts illustrated hereinafter are suitable for use in the instant compositions and may be desirably incorporated in certain aspects of the invention, for example to assist or enhance performance, A variety of optional ingredients can also be added to hair care compositions. Optional ingredients can include, but are not limited to, structurants, humectants, fatty acids, inorganic salts, and other antimicrobial agents or actives.

A hair care composition can also include hydrophilic structurants such as carbohydrate structurants and gums. Some suitable carbohydrate structurants include raw starch (corn, rice, potato, wheat, and the like) and pregelatinized starch. Some suitable gums include carregeenan and xanthan gum. A hair care composition can include from about 0.1% to about 30%, from about 2% to about 25%, or from about 4% to about 20%, by weight of the hair care composition, of a carbohydrate structurant.

A hair care composition can also include one or more humectants. Examples of such humectants can include polyhydric alcohols. Further, humectants such as glycerin can be included the hair care composition as a result of production or as an additional ingredient. For example, glycerin can be a by-product after saponification of the hair care composition. Including additional humectant can result in a number of benefits such as improvement in hardness of the hair care composition, decreased water activity of the hair care composition, and reduction of a weight loss rate of the hair care composition over time due to water evaporation.

A hair care composition can include inorganic salts. Inorganic salts can help to maintain a particular water content or level of the hair care composition and improve hardness of the hair care composition. The inorganic salts can also help to bind the water in the hair care composition to prevent water loss by evaporation or other means. A hair care composition can optionally include from about 0.01% to about 15%, from about 1% to about 12%, or from about 2.5% to about 10.5%, by weight of the hair care composition, of inorganic salt. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

A hair care composition can include one or more additional antibacterial agents that can serve to further enhance antimicrobial effectiveness of the hair care composition. A hair care composition can include, for example, from about 0.001% to about 2%, from about 0.01% to about 1.5%, or from about 0.1% to about 1%, by weight of the hair care composition, of additional antibacterial agent(s). Examples of suitable antibacterial agents can include carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids. Other suitable antibacterial agents are described in U.S. Pat. No. 6,488,943.

Scalp Active Material

In an embodiment of the present invention, the hair care composition may comprise a scalp active material, which may be an anti-dandruff active. In an embodiment, the anti-dandruff active is selected from the group consisting of: pyridinethione salts; zinc carbonate; azoles, such as ketoconazole, econazole, and elubiol; selenium sulfide; particulate sulfur; keratolytic agents such as salicylic acid; and mixtures thereof. In a further embodiment, the anti-dandruff active may be an anti-dandruff particulate. In an embodiment, the anti-dandruff particulate is a pyridinethione salt. Such anti-dandruff particulate should be physically and chemically compatible with the components of the composition, and should not otherwise unduly impair product stability, aesthetics or performance.

In an embodiment of the present invention, the selenium sulfide is present from about about 0.01% to about 10%, in an embodiment from about 0.1% to about 8%, in a further embodiment, from about 1% to about 5%.

In an embodiment of the present invention, the sulfur is present from about 0.01% to about 10%, in an embodiment from about 0.1% to about 8%, in a further embodiment, from about 1% to about 5% and from about 2% to about 5%.

Pyridinethione particulates are suitable particulate anti-dandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753, 196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, charcoal, whitfield's ointment, castellani's paint, aluminum chloride, gentian violet, octopirox (piroctone olamine), ciclopirox olamine, undecylenic acid and its metal salts, potassium permanganate, selenium sulfide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulfide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+} A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{+x}(OH)_{3(1-y)}]^+ A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+}$ 2 x $A^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

Hair Care Compositions

Exemplary hair care rinse-off hair care compositions can include an aqueous carrier, which can be present at a level of from about 5% to about 95%, or from about 60% to about 85%. The aqueous carrier may comprise water, or a miscible mixture of water and organic solvent. Non-aqueous carrier materials can also be employed.

In an embodiment of the present invention, a surfactant may be present in the range of about 0.1% to about 40%, in a further embodiment, from about 0.5% to about 30%, in a further embodiment, from about 1% to about 25%.

Such rinse-off hair care compositions can include one or more detersive surfactants. The detersive surfactant component can be included to provide cleaning performance to the product. The detersive surfactant component in turn comprises anionic detersive surfactant, zwitterionic or amphoteric detersive surfactant, or a combination thereof. A representative, non-limiting, list of anionic surfactants includes anionic detersive surfactants for use in the compositions can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the anionic surfactant can be sodium lauryl sulfate or sodium laureth sulfate. The concentration of the anionic surfactant component in the product can be sufficient to provide a desired cleaning and/or lather performance, and generally ranges from about 2% to about 40%.

Amphoteric detersive surfactants suitable for use in the rinse-off hair care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off hair care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

In a further embodiment of the present invention, the hair care composition may comprise an cationic surfactant.

The liquid rinse off hair care composition can comprise one or more phases. Such hair care compositions can include a cleansing phase and/or a benefit phase (i.e., a single- or multi-phase composition). Each of a cleansing phase or a benefit phase can include various components. The cleansing phase and the benefit phase can be blended, separate, or a combination thereof. The cleansing phase and the benefit phase can also be patterned (e.g. striped).

The cleansing phase of a hair care composition can include at least one surfactant. The cleansing phase can be an aqueous structured surfactant phase and constitute from about 5% to about 20%, by weight of the hair care composition. Such a structured surfactant phase can include sodium trideceth(n) sulfate, hereinafter STnS, wherein n can define average moles of ethoxylation. n can range, for example, from about 0 to about 3; from about 0.5 to about 2.7, from about 1.1 to about 2.5, from about 1.8 to about 2.2, or n can be about 2. When n can be less than 3, STnS can provide improved stability, improved compatibility of benefit agents within the hair care compositions, and increased mildness of the compositions as disclosed in U.S. Pre-Grant Publication No. 2010/009285 A1.

The cleansing phase can also comprise at least one of an amphoteric surfactant and a zwitterionic surfactant. Suitable amphoteric or zwitterionic surfactants (in addition to those cited herein) can include, for example, those described in U.S. Pat. Nos. 5,104,646 and 5,106,609.

A cleansing phase can comprise a structuring system. A structuring system can comprise, optionally, a non-ionic emulsifier, optionally, from about 0.05% to about 5%, by weight of the hair care composition, of an associative polymer, and an electrolyte.

The hair care composition can optionally be free of sodium lauryl sulfate, hereinafter SLS, and can comprise at least a 70% lamellar structure. However, the cleansing phase could comprise at least one surfactant, wherein the at least one surfactant includes SLS. Suitable examples of SLS are described in U.S. Pre-Grant Publication No. 2010/0322878 A1.

Rinse-off hair care compositions can also include a benefit phase. The benefit phase can be hydrophobic and/or anhydrous. The benefit phase can also be substantially free of surfactant. A benefit phase can also include a benefit agent. In particular, a benefit phase can comprise from about 0.1% to about 50% benefit agent by weight of the hair care composition. The benefit phase can alternatively comprise less benefit agent, for example, from about 0.5% to about 20% benefit agent, by weight of the hair care composition. Examples of suitable benefit agents can include petrolatum, glyceryl monooleate, mineral oil, natural oils, and mixtures thereof. Additional examples of benefit agents can include water insoluble or hydrophobic benefit agents. Other suitable benefit agents are described in U.S. Pre-Grant Publication No. 2012/0009285 A1.

Non-limiting examples of glycerides suitable for use as hydrophobic hair benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic hair benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic hair benefit agents herein can include decaglyceryl distearate, decaglyceryl diisostearate, decaglyceryl monomyriate, decaglyceryl monolaurate, hexaglyceryl monooleate, and combinations thereof.

Rinse-Off Conditioner Composition

The conditioner composition described herein comprises a sum of total 0.0001% to about 2% of alpha,alpha,6,6-tetramethylbicyclo[3.1.1]hept-2-ene-propanal) and one or more malodor reduction materials having a Sulfur MORV>3; b) from about 0.01% to about 10% of selenium sulfide; and from about 0.1% to about 10% of a cationic surfactant or a mixture of cationic surfactants and an aqueous carrier. The conditioner composition may also comprise a conditioner gel matrix comprising part or all of the cationic surfactant, whereas the conditioner gel network may also comprise one or more high melting point fatty compounds (i.e. fatty alcohols), and an second aqueous carrier.

The conditioner gel matrix of the conditioner composition includes a cationic surfactant or a cationic surfactant system. The cationic surfactant system can be selected from: mono-long alkyl quaternized ammonium salt; a combination of mono-long alkyl quaternized ammonium salt and di-long alkyl quaternized ammonium salt; mono-long alkyl amido-amine salt; a combination of mono-long alkyl amidoamine salt and di-long alkyl quaternized ammonium salt, a combination of mono-long alkyl amindoamine salt and mono-long alkyl quaternized ammonium salt. The cationic surfactant system can be included in the composition at a level by weight of from about 0.1% to about 10%, from about 0.5% to about 8%, from about 0.8% to about 5%, and from about 1.0% to about 4%.

The conditioner gel matrix of the conditioner composition includes one or more high melting point fatty compounds. Suitable fatty alcohols include, for example, cetyl alcohol, stearyl alcohol, behenyl alcohol, and mixtures thereof. The high melting point fatty compound can be included in the conditioner composition at a level of from about 0.1% to about 20%, alternatively from about 1% to about 15%, and alternatively from about 1.5% to about 8% by weight of the composition. The conditioner gel matrix of the conditioner composition includes a second aqueous carrier. The second aqueous carrier may comprise water, or a miscible mixture of water and organic solvent.

Leave-on Treatment Composition

The leave-on treatment composition described herein comprises a sum of total 0.0001% to about 2% of alpha, alpha,6,6-tetramethylbicyclo[3.1.1]hept-2-ene-propanal) and one or more malodor reduction materials having a Sulfur MORV>3; b) from about 0.01% to about 10% of selenium sulfide; and from about 0.1% to about 10% of a cationic surfactant or a mixture of cationic surfactants and an aqueous carrier. The leave-on treatment may also comprise one or more rheology modifiers and a third aqueous carrier.

In one embodiment the leave-on treatment may include a conditioner gel matrix as described above (in the rinse-off conditioner description).

In another embodiment the leave-on treatment may include one or more rheology modifiers. Any suitable rheology modifier can be used. In an embodiment, the leave-on treatment may comprise from about 0.01% to about 3% of a rheology modifier, alternatively from about 0.1% to about 1% of a rheology modifier, Additional Components The conditioner compositions, and/or leave-on treatments described herein may optionally comprise one or more additional components known for use in hair care or personal care products, Non-limiting examples of additional components for use in the hair care compositions include conditioning agents (silicone or non-silicone conditioning agents), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

The rinse-off hair care composition can be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device can help delivery of the particulate antimicrobial agent to target regions, such as, for example, hair follicles and undulations that can exist in the underarm. The rinse-off care product can be sold together with such an implement or device. Alternatively, an implement or device can be sold separately but contain indicium to indicate usage with a rinse-off care product. Implements and delivery devices can employ replaceable portions (e.g., the skin interaction portions), which can be sold separately or sold together with the rinse-off care product in a kit.

Test Methods

Malodor reduction materials may be separated from mixtures, including but not limited to finished products such as consumer products and identified, by analytical methods that include GC-MS and/or NMR.

Test Method for Determining Saturation Vapour Pressure (VP)

The saturation Vapour Pressure (VP) values are computed for each PRM in the perfume mixture being tested. The VP of an individual PRM is calculated using the VP Computational Model, version 14.02 (Linux) available from Advanced Chemistry Development Inc. (ACD/Labs) (Toronto, Canada) to provide the VP value at 25° C. expressed in units of torr. The ACD/Labs' Vapor Pressure model is part of the ACD/Labs model suite.

Test Method for Determining the Logarithm of the Octanol/Water Partition Coefficient (log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Test Method for the Generation of Molecular Descriptors

In order to conduct the calculations involved in the computed-value test methods described herein, the starting information required includes the identity, weight percent, and molar percent of each PRM in the perfume being tested, as a proportion of that perfume, wherein all PRMs in the perfume composition are included in the calculations. Additionally for each of those PRMs, the molecular structure, and the values of various computationally-derived molecular descriptors are also required, as determined in accordance with the Test Method for the Generation of Molecular Descriptors described herein.

For each PRM in a perfume mixture or composition, its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each PRM. For PRMs, which at the time of their testing are not yet listed in the CAS Chemical Registry System database, other databases or information sources may be used to determine their structures. For a PRM which has potentially more than one isomer present, the molecular descriptor computations are conducted using the molecular structure of only one of the isomers, which is selected to represent that PRM. The selection of isomer is determined by the relative amount of extension in the molecular structures of the isomers. Of all the isomers of a given PRM, it is the isomer whose molecular structure that is the most prevalent which is the one that is selected to represent that PRM. The structures for other potential isomers of that PRM are excluded from the computations. The molecular structure of the isomer that is the most prevalent is paired with the concentration of that PRM, where the concentration reflects the presence of all the isomers of that PRM that are present.

A molecule editor or molecular sketching software program, such as ChemDraw (CambridgeSoft/PerkinElmer Inc., Waltham, Mass., U.S.A.), is used to duplicate the 2-dimensional molecular structure representing each PRM. Molecular structures should be represented as neutral species (quaternary nitrogen atoms are allowed) with no disconnected fragments (e.g., single structures with no counter ions). The winMolconn program described below can convert any deprotonated functional groups to the neutral form by adding the appropriate number of hydrogen atoms and will discard the counter ion.

For each PRM, the molecular sketching software is used to generate a file which describes the molecular structure of the PRM. The file(s) describing the molecular structures of the PRMs is subsequently submitted to the computer software program winMolconn, version 1.0.1.3 (Hall Associates Consulting, Quincy, Mass., U.S.A., www.molconn.com), in order to derive various molecular descriptors for each PRM. As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a ".smi" or ".txt" file name extension. The SDF file represents each molecular structure in the format of a multi-line record, while the syntax for a SMILES structure is a single line of text with no white space. A structure name or identifier can be added to the SMILES string by including it on the same line following the SMILES string and separated by a space, e.g.: C1=CC=CC=C1 benzene.

The winMolconn software program is used to generate numerous molecular descriptors for each PRM, which are then output in a table format. Specific molecular descriptors derived by winMolconn are subsequently used as inputs (i.e., as variable terms in mathematical equations) for a variety of computer model test methods in order to calculate values such as: saturation Vapour Pressure (VP); Boiling Point (BP); logarithm of the Octanol/Water Partition Coefficient (log P); Odour Detection Threshold (ODT); Malodour Reduction Value (MORV); and/or Universal Malodour Reduction Value (Universal MORV) for each PRM. The molecular descriptor labels used in the models' test method computations are the same labels reported by the winMolconn program, and their descriptions and definitions can be found listed in the winMolconn documentation. The following is a generic description of how to execute the winMolconn software program and generate the required molecular structure descriptors for each PRM in a composition.

Computing Molecular Structure Descriptors using winMolconn:
1) Assemble the molecular structure for one or more perfume ingredients in the form of a MACCS Structure-Data File, also called an SDF file, or as a SMILES file.
2) Using version 1.0.1.3 of the winMolconn program, running on an appropriate computer, compute the full complement of molecular descriptors that are available from the program, using the SDF or SMILES file described above as input.
   a. The output of winMolconn is in the form of an ASCII text file, typically space delimited, containing the structure identifiers in the first column and respective molecular descriptors in the remaining columns for each structure in the input file.
3) Parse the text file into columns using a spreadsheet software program or some other appropriate technique. The molecular descriptor labels are found on the first row of the resulting table.
4) Find and extract the descriptor columns, identified by the molecular descriptor label, corresponding to the inputs required for each model.
   a. Note that the winMolconn molecular descriptor labels are case-sensitive.

MORV Calculation
1.) Input Molecular Descriptor values as determined via the method above into the following equation:

$$MORV = -0.0035 + 0.8028 \times (SHCsatu) + 2.1673 \times (xvp7) - 1.3507 \times (c1C1C3d) + 0.61496 \times (c1C1O2) + 0.00403 \times (idc) - 0.23286 \times (nd2).$$

This equation relates a material's effectiveness in reducing the malodor 3-mercapto-3-methylhexan-1-ol (thiol based malodors)

2.) For purpose of the present application, a material's MORV is the highest MORV value from the above equation. The purpose of this experimental design is to determine whether malodor reducing compositions show benefit in reducing the perception of malodor from selenium sulfide-containing shampoos.

Procedure:
Six malodor reduction accords are dosed into unperfumed selenium sulfide shampoo at 4 different levels; samples are allowed to equilibrate at room temperature for at least 1 week before evaluating.

1 Malodor Reduction Composition (MRC)

| CAS | MATERIAL | Wt % |
| --- | --- | --- |
| 13877-91-3 | (3Z)-3,7-dimethylocta-1,3,6-triene | 3.000 |
| 5413-60-5 | (3a,4,5,6,7,7a-hexahydro-1H-4,7-methanoinden-6-yl acetate t | 10.000 |
| 33885-52-8 | alpha,alpha,6,6-tetramethyl bicyclo[3.1.1]hept-2-ene-propanal) | 1.500 |
| 23787-90-8 | 1,3,4,6,7,8alpha-hexahydro-1,1,5,5-tetramethyl-2H-2,4alpha-methanophtalen-8(5H)-one | 14.000 |
| 4430-31-3 | 3,4,4a,5,6,7,8,8a-octahydrochromen-2-one | 10.000 |
| 300371-33-9 | 2,3-dihydro-1,1-1H-dimethyl-indene-ar-propanal | 1.500 |
| 55066-48-3 | 3-methyl-5-phenylpentan-1-ol | 10.000 |

-continued

| CAS | MATERIAL | Wt % |
|---|---|---|
| 139504-68-0 | 1-((2-(tert-butyl)cyclohexyl)oxy)butan-2-ol | 10.000 |
| 3681-73-0 | (E)-3,7-dimethylocta-2,6-dien-1-yl palmitate) | 40.000 |

2 Malodor Reduction Composition (MRC)

| CAS | MATERIAL | Wt % |
|---|---|---|
| 58430-94-7 | 3,5,5-trimethylhexyl acetate | 56 |
| 33885-52-8 | alpha,alpha,6,6-tetramethyl bicyclo[3.1.1]hept-2-ene-propanal) | 18 |
| 1139-30-6 | 4,5-epoxy-4,11,11-trimethyl-8-methylenebicyclo(7.2.0)undecane | 0.5 |
| 27606-09-3 | 2,4-dimethyl-4,4a,5,9b-tetrahydroindeno[1,2-d][1,3]dioxine | 15 |
| 127-42-4 | (E)-1-(2,6,6-trimethyl-1-cyclohex-2-enyl)pent-1-en-3-one | 2 |
| 23787-90-8 | (1,3,4,6,7,8alpha-hexahydro-1,1,5,5-tetramethyl-2H-2,4alpha-methanophtalen-8(5H)-one | 5 |
| 68912-13-0 | 8,8-dimethyl-3a,4,5,6,7,7a-hexahydro-1H-4,7-methanoinden-6-yl propionate | 3.5 |

3 Malodor Reduction Composition (MRC)

| CAS | MATERIAL | Wt % |
|---|---|---|
| 5413-60-5 | (3a,4,5,6,7,7a-hexahydro-1H-4,7-methanoinden-6-yl acetate | 15.000 |
| 23787-90-8 | 1,3,4,6,7,8alpha-hexahydro-1,1,5,5-tetramethyl-2H-2,4alpha-methanophtalen-8(5H)-one | 5.000 |
| 300371-33-9 | 2,3-dihydro-1,1-1H-dimethyl-indene-ar-propanal | 1.000 |
| 55066-48-3 | 3-methyl-5-phenylpentan-1-ol | 49.000 |
| 139504-68-0 | 1-((2-(tert-butyl)cyclohexyl)oxy)butan-2-ol | 10.000 |
| 3681-73-0 | (E)-3,7-dimethylocta-2,6-dien-1-yl palmitate) | 20.000 |

4 Malodor Reduction Composition (MRC)

| CAS | MATERIAL | Wt % |
|---|---|---|
| 23787-90-8 | 1,3,4,6,7,8alpha-hexahydro-1,1,5,5-tetramethyl-2H-2,4alpha-methanophtalen-8(5H)-one | 40.000 |
| 300371-33-9 | 2,3-dihydro-1,1-1H-dimethyl-indene-ar-propanal | 10.000 |
| 55066-48-3 | 3-methyl-5-phenylpentan-1-ol | 10.000 |
| 3681-73-0 | (E)-3,7-dimethylocta-2,6-dien-1-yl palmitate) | 40.000 |

5 Malodor Reduction Composition (MRC)

| CAS | MATERIAL | Wt % |
|---|---|---|
| 58430-94-7 | 3,5,5-trimethylhexyl acetate | 2.05 |
| 98-52-2 | 4-tert-butyl cyclohexane | 0.25 |
| 32210-23-4 | 4-(tert-butyl)cyclohexyl acetate | 7.6 |
| 30772-79-3 | Octahydro-1H-4,7-methanoindene-1-carbaldehyde | 0.28 |
| 63500-71-0 | 2-isobutyl-4-hydroxy-4-methyltetrahydropyran 1 | 9.5 |
| 101-84-8 | DIPHENYL OXIDE | 0.28 |
| 19870-74-7 | Cedryl Methyl Ether | 62.2 |
| 23787-90-8 | (1,3,4,6,7,8alpha-hexahydro-1,1,5,5-tetramethyl-2H-2,4alpha-methanophtalen-8(5H)-one | 9.5 |
| 93-16-3 | (Z)-1,2-dimethoxy-4-(prop-1-en-1-yl)benzene | 4.46 |
| 55066-48-3 | 3-methyl-5-phenylpentan-1-ol | 3.8 |
| 24851-98-7 | methyl 2-(3-oxo-2-pentylcyclopentyl)acetate | 0.08 |

6 Malodor Reduction Composition (MRC)

| CAS | MATERIAL | Wt % |
|---|---|---|
| 58430-94-7 | 3,5,5-trimethylhexyl acetate | 40 |
| 5413-60-5 | (3a,4,5,6,7,7a-hexahydro-1H-4,7-methanoinden-6-yl acetate | 20 |
| 23787-90-8 | 1,3,4,6,7,8alpha-hexahydro-1,1,5,5-tetramethyl-2H-2,4alpha-methanophtalen-8(5H)-one | 20 |
| 300371-33-9 | 2,3-dihydro-1,1-1H-dimethyl-indene-ar-propanal | 10 |
| 55066-48-3 | 3-methyl-5-phenylpentan-1-ol | 10 |

Samples to a depth of ~1 cm are placed into plastic cups; cups are covered with lids, then lids are removed for evaluation. Each sample is evaluated by 4 trained odor panelists for the presence of sulfur malodor. The unperfumed shampoo with no Malodor Reduction Composition (MRC) is set as positive control (ie, "2") while a separate batch of the same shampoo formula, sans selenium sulfide, is set as negative control (ie, "0"). Additionally, a 50:50 blend of the 2 unperfumed shampoos (with and without selenium sulfide) is created and this is set as an additional "low sulfur" benchmark for improved coverage (Ie, "1"). Sample presentation is randomized.

Instructions are provided to the panelists as follows:
1) Please smell sample labeled "Control". Note the amount of sulfur base odor. This is your benchmark for subsequent evaluations. You can also refer to "Low Sulfur Control" and "No Sulfur Control" as needed, however, the scale is relative to "Control".
2) Please evaluate each sample by removing the lid, and indicate the amount of sulfur relative to the control that you can detect in each sample. You may or may not be able to smell perfume materials in the test samples; please assess only for amount of sulfur odor using the scale below:
   0=I cannot smell any sulfur odor at all (you can refer to "No Sulfur Control")
   1=I smell some sulfur odor, but less than the "control" (You can refer to "Low Sulfur Control)
   2=I smell sulfur odor equal to the control 3=I smell more sulfur odor than in the control
Panelists evaluate each level series as a set, taking a break in between sets to avoid olfactive saturation.
Results
Round 1-0.01% Malodor
Reduction Composition (MRC)

|       | Panelist 1 | Panelist 2 | Panelist 3 | Panelist 4 | Avg |
|-------|------------|------------|------------|------------|-------|
| MRC 1 | 1 | 0 | 1 | 0.5 | 0.625 |
| MRC 2 | 1 | 0 | 0 | 0.5 | 0.375 |
| MRC 3 | 1 | 1 | 2 | 1 | 1.25 |
| MRC 4 | 1 | 2 | 1 | 2 | 1.5 |
| MRC 5 | 2 | 1.5 | 1 | 2 | 1.625 |
| MRC 6 | 1 | 1 | 1 | 1 | 1 |

Round 2-0.05% Malodor

Reduction composition (MRC)

| | | | | | |
|---|---|---|---|---|---|
| MRC 1 | 0 | 1 | 2 | 0 | 0.75 |
| MRC 2 | 0 | 1 | 0.5 | 0 | 0.375 |
| MRC 3 | 1 | 1.5 | 1 | 1 | 1.125 |
| MRC 4 | 0 | 2 | 1 | 1 | 1 |
| MRC 5 | 0 | 2 | 2 | 2 | 1.5 |
| MRC 6 | 0 | 2 | 2 | 1 | 1.25 |

Round 3-0.1% Malodor

Reduction composition (MRC)

| | | | | | |
|---|---|---|---|---|---|
| MRC 1 | 1 | 0 | 1 | 1 | 0.75 |
| MRC 2 | 0 | 0 | 0 | 0 | 0 |
| MRC 3 | 1 | 0 | 0 | 1 | 0.5 |
| MRC 4 | 0 | 1 | 1 | 1 | 0.75 |
| MRC 5 | 1 | 0.5 | 2 | 2 | 1.375 |
| MRC 6 | 0 | 1 | 2 | 1 | 1 |

Round 4-0.15% Malodor

Reduction composition (MRC)

| | | | | | |
|---|---|---|---|---|---|
| MRC 1 | 1 | 0 | 1.5 | 1 | 0.875 |
| MRC 2 | 0 | 1 | 0.5 | 0 | 0.375 |
| MRC 3 | 0 | 1 | 2 | 1 | 1 |
| MRC 4 | 0 | 1 | 1 | 1 | 0.75 |
| MRC 5 | 0 | 2 | 2 | 1 | 1.25 |
| MRC 6 | 1 | 1 | 1 | 1 | 1 |

Summary
MRC 1, MRC 2, MRC 3 and MRC 4 all show considerable reduction (<1 Avg) in perceived sulfur levels at one or more levels tested. Additionally, MRC 2 showed reduction at all levels tested, with all panelists assigning a zero or "no sulfur" rating at the 0.1% added level.

As a follow up, the MRC 2 is diluted in 100 deg F. tap water at a ratio of 1 ml shampoo to 75 ml water; these samples are placed into cups, capped, and agitated until the shampoo is dissolved. They are immediately evaluated by 2 panelists to determine if sulfur odor is present in the dilute samples.

|  | Panelist 1 | Panelist 4 |
|---|---|---|
| MRC 2 @ 0.01%, diluted 1:75 in warm water (100 F.) | 1 | 1.5 |
| MRC 2 @ 0.05%, diluted 1:75 in warm water (100 F.) | 0.5 | 0.5 |
| MRC 2 @ 0.10%, diluted 1:75 in warm water (100 F.) | 0 | 0 |
| MRC 2 @ 0.15%, diluted 1:75 in warm water (100 F.) | 0 | 0 |

In dilution, the perceived benefit holds, particularly at the 0.1% and 0.15% levels.

Conclusion

Malodor Reduction Composition's demonstrates effectiveness in the masking/blocking of selenium sulfide odor. In the present invention, this understanding can be leveraged in formulation strategies for selenium sulfide containing hair care compositions.

I. Hair Switch Selection and Preparation—for Ah Tests
   a) For each product, a 20 gram hair switch is used, cleaned and stripped of perfume. Cleaning may be done via external vendor (ie, ATL 2× baking soda/main mix) or internally via local documented procedures. (New hair switches can be pre-washed with unperfumed shampoo before very first use)
   b) Each hair switch is evaluated before each use to ensure no contamination/off odors.

II. Shampoo Fragrance Profile
   a) A neat product is evaluated; and a neat sulfur score is recorded
   b) The water temperature may be adjusted to 100 F/38 C and 1.5 gal/5.7 l per min; and hair is wetted for 20 seconds.
   c) 2 ml product is applied; and lather is produced for 30 seconds.
   d) Odor is evaluated using sulfur scoring and comments are recorded.

TABLE 4

Evaluate MRC2 On Switch vs Negative Control
In-Use Evaluation 20 gram hair switch used, 2 ml product;
100 F. water according to the method described above.

| Product | Sulfur Odor Neat Scale (0-3) | Neat Comments | Lather Sulfur Scale (0-3) | Lather Comments |
|---|---|---|---|---|
| Selenium Sulfide Unperfumed Shampoo | 2 | sulfur odor | 2 | sulfur odor |
| Non Malodor Reducing Accord[1] @ 0.1% in Selenium Sulfide Shampoo | 1 | sulfur odor + rose powdery note | 1 | sulfur odor + rose powdery note |
| MRC2 @ 0.1% in Selenium Sulfide Shampoo | 0 | ozonic, floral | 0 | ozonic. Floral |

TABLE 4-continued

Evaluate MRC2 On Switch vs Negative Control
In-Use Evaluation 20 gram hair switch used, 2 ml product;
100 F. water according to the method described above.

1. Non-Malodor Reducing Accord

| Material | % | CAS |
| --- | --- | --- |
| Citronellol | 20 | 106-22-920 |
| Linalool | 30 | 78-70-6 |
| Phenyl Ethyl Alcohol | 50 | 60-12-8 |

Sulfur Odor Scale:
0 = I cannot smell any sulfur odor at all (you can refer to "No Sulfur Control")
1 = I smell some sulfur odor, but less than the "control" (You can refer to "Low Sulfur Control")
2 = I smell sulfur odor equal to the control
3 = I smell more sulfur odor than in the control

TABLE 5

Evaluate MRC 2 On Switch vs non malodor reducing accord-0.01% Levels
In-Use Evaluation 20 gram hair switch used, 2 ml product;
100 F. water according to the method described above.

| Product | Neat Sulfur Odor Scale (0-3) | Neat Comments | Lather Sulfur Scale (0-3) | Lather Comments |
| --- | --- | --- | --- | --- |
| Selenium Sulfide Unperfumed Shampoo | 2 | sulfur odor | 2 | sulfur odor |
| Non- malodor reducing accord[1] @ 0.01% in Selenium Sulfide Shampoo (ref batch | 1.5 | slight rosy, noticeable sulfur | 2 | sulfur odor |
| MBRC 2 @ 0.01% in Selenium Sulfide Shampoo | 0.5 | slight ozonic, very slight sulfur | 0.5 | Slight ozonic, very slight sulfur |

1. Non-Malodor Reducing Accord

| Material | % | CAS |
| --- | --- | --- |
| Citronellol | 20 | 106-22-920 |
| Linalool | 30 | 78-70-6 |
| Phenyl Ethyl Alcohol | 50 | 60-12-8 |

Sulfur Odor Scale:
0 = I cannot smell any sulfur odor at all (you can refer to "No Sulfur Control")
1 = I smell some sulfur odor, but less than the "control" (You can refer to "Low Sulfur Control")
2 = I smell sulfur odor equal to the control
3 = I smell more sulfur odor than in the control

Conclusion

This series of experiments indicates that malodor reducing ingredients or a combination of those, such as MRC2, provides a malodor blocking benefit both in neat product and during the lather phase. This benefit goes beyond the masking benefit that would be provided by a non-malodor reducing perfume. In table 4 (0.1% data), the non-malodor reducing accord exhibits malodor interference via masking benefit due to the perfume intensity imparted by the ingredients. In table 5 (the 0.01% data) it is demonstrated that as level is reduced the masking benefit of the non-malodor-reducing accord is decreased, while the malodor blocking property of the MRC2 is maintained.

Examples Shampoo with Malodor Reducing Composition

An example of Shampoo compositions prepared with malodor reduction composition, according to the compositions shown in Example 1.

| Ingredient | 1 | 2 | 3 |
| --- | --- | --- | --- |
| | Wt % | | |
| Ammonium Laureth Sulfate[1] | 14.1 | 14.1 | 14.1 |
| Ammonium Lauryl Sulfate[2] | 3.1 | 3.1 | 3.1 |
| Ammonium Xylenesulfonate[3] | 0.45 | 0.45 | 0.45 |
| TWEEN 60[4] | 3.0 | 3.0 | 3.0 |
| Polyquaternium-10[5] | 0.35 | 0.35 | 0.35 |
| Cetrimonium Chloride[6] | 0.5 | 0.5 | 0.5 |
| Selenium Sulfide[7] | 1.0 | 1.0 | 1.0 |
| Dimethicone[8] | 0.60 | 0.60 | 0.60 |
| Ethylene Glycol Distearate[9] | 3.0 | 3.0 | 3.0 |
| Cocamide MEA[10] | 3.0 | 3.0 | 3.0 |
| Zinc Pyrithione[11] | — | 0.2 | 0.2 |
| Zinc Carbonate[12] | — | — | 1.61 |
| Neat Fragrance | 1.1 | 0.75 | 0.75 |
| Malodor reducing composition | 0.25 | 0.25 | 0.175 |
| Cetyl Alcohol[13] | 0.42 | 0.42 | 0.42 |
| DMDM Hydantoin | 0.40 | 0.40 | 0.40 |
| Sodium Chloride | 0.30 | 0.30 | 0.30 |
| Stearyl Alcohol[14] | 0.20 | 0.20 | 0.20 |

| Ingredient | 1 | 2 | 3 |
|---|---|---|---|
| | | Wt % | |
| Hydroxypropyl Methylcellulose[15] | 0.02 | 0.02 | 0.02 |
| Water | Q.S. | Q.S. | Q.S. |

[1] Ammonium Laureth Sulfate at 25% active, supplier: P&G
[2] Ammonium Lauryl Sulfate at 25% active, supplier: P&G
[3] Ammonium Xylene Sulfonate 40% active, supplier: Stepan
[4] Polysorbate 60, upplier: Croda
[5] UCARE Polymer LR400, supplier- Dow Chemical
[6] cetrimonium chloride, supplier - Croda
[7] Selenium disulfide, supplier Eskay
[8] Viscasil 330M from Momentive Performance Materials with a viscosity of 330,000 cSt (centistokes).
[9] Ethylene Glycol Disterate, supplier: Stepan
[10] Ninol COMF from the Stepan Company
[11] Zinc Pyrithione, supplier Lonza
[12] Zinc Carbonate Basic, supplier Pan Continental Chemical
[13] Cetyl Alcohol, supplier P&G
[14] Stearyl Alcohol, supplier P&G
[15] Methocel, supplier Dow Chemical

| Ingredient | 4 | 5 | 6 |
|---|---|---|---|
| | | Wt % | |
| Ammonium Laureth Sulfate[1] | 14.1 | 14.1 | 14.1 |
| Ammonium Lauryl Sulfate[2] | 3.1 | 3.1 | 3.1 |
| Ammonium Xylenesulfonate[3] | 0.45 | 0.45 | 0.45 |
| TWEEN 60[4] | 3.0 | 3.0 | 3.0 |
| Polyquaternium-10[5] | 0.35 | 0.35 | 0.35 |
| Cetrimonium Chloride[6] | 0.5 | 0.5 | 0.5 |
| Selenium Sulfide[7] | 1.0 | 0.2 | 0.2 |
| Dimethicone[8] | 0.60 | 0.60 | 0.60 |
| Ethylene Glycol Distearate[9] | 3.0 | 3.0 | 3.0 |
| Cocamide MEA[10] | 3.0 | 3.0 | 3.0 |
| Zinc Pyrithione[11] | — | 1.0 | 1.0 |
| Zinc Carbonate[12] | — | — | 1.61 |
| Neat Fragrance | 0.65 | 0.85 | 1.0 |
| Malodor reducing composition | 0.175 | 0.175 | 0.175 |
| Cetyl Alcohol[13] | 0.42 | 0.42 | 0.42 |
| DMDM Hydantoin | 0.40 | 0.40 | 0.40 |
| Sodium Chloride | 0.30 | 0.30 | 0.30 |
| Stearyl Alcohol[14] | 0.20 | 0.20 | 0.20 |
| Hydroxypropyl Methylcellulose[15] | 0.02 | 0.02 | 0.02 |
| Water | Q.S. | Q.S. | Q.S. |

[1] Ammonium Laureth Sulfate at 25% active, supplier: P&G
[2] Ammonium Lauryl Sulfate at 25% active, supplier: P&G
[3] Ammonium Xylene Sulfonate 40% active, supplier: Stepan
[4] Polysorbate 60, upplier: Croda
[5] UCARE Polymer LR400, supplier- Dow Chemical
[6] cetrimonium chloride, supplier - Croda
[7] Selenium disulfide, supplier Eskay
[8] Viscasil 330M from Momentive Performance Materials with a viscosity of 330,000 cSt (centistokes).
[9] Ethylene Glycol Disterate, supplier: Stepan
[10] Ninol COMF from the Stepan Company
[11] Zinc Pyrithione, supplier Lonza
[12] Zinc Carbonate Basic, supplier Pan Continental Chemical
[13] Cetyl Alcohol, supplier P&G
[14] Stearyl Alcohol, supplier P&G
[15] Methocel, supplier Dow Chemical In an embodiment of the present invention, the example of Shampoo compositions (Example 5) may also be prepared with the malodor reduction composition according to the compositions shown in Example 2 and/or Example 3.

| Ingredient | 7 | 8 | 9 |
|---|---|---|---|
| | | Wt % | |
| Ammonium Laureth Sulfate[1] | 14.1 | 14.1 | 14.1 |
| Ammonium Lauryl Sulfate[2] | 3.1 | 3.1 | 3.1 |
| Ammonium Xylenesulfonate[3] | 0.45 | 0.45 | 0.45 |
| TWEEN 60[4] | 3.0 | 3.0 | 3.0 |
| Polyquaternium-10[5] | 0.35 | 0.35 | 0.35 |
| Cetrimonium Chloride[6] | 0.5 | 0.5 | 0.5 |
| Sulfur[7] | 2.0 | 5.0 | 3.5 |
| Dimethicone[8] | 0.60 | 0.60 | 0.60 |
| Ethylene Glycol Distearate[9] | 3.0 | 3.0 | 3.0 |
| Cocamide MEA[10] | 3.0 | 3.0 | 3.0 |
| Selenium Sulfide[11] | — | — | — |
| Neat Fragrance | 0.85 | 1.1 | 0.95 |
| Malodor reducing composition | 0.175 | 0.25 | 0.25 |
| Cetyl Alcohol[12] | 0.42 | 0.42 | 0.42 |
| DMDM Hydantoin | 0.40 | 0.40 | 0.40 |
| Sodium Chloride | 0.30 | 0.30 | 0.30 |
| Stearyl Alcohol[13] | 0.20 | 0.20 | 0.20 |
| Hydroxypropyl Methylcellulose[14] | 0.02 | 0.02 | 0.02 |
| Water | Q.S. | Q.S. | Q.S. |

[1] Ammonium Laureth Sulfate at 25% active, supplier: P&G
[2] Ammonium Lauryl Sulfate at 25% active, supplier: P&G
[3] Ammonium Xylene Sulfonate 40% active, supplier: Stepan
[4] Polysorbate 60, upplier: Croda
[5] UCARE Polymer LR400, supplier- Dow Chemical
[6] cetrimonium chloride, supplier - Croda
[7] Sulfur USP, supplier Universal Preserv-A-Chem
[8] Viscasil 330M from Momentive Performance Materials with a viscosity of 330,000 cSt (centistokes).
[9] Ethylene Glycol Disterate, supplier: Stepan
[10] Ninol COMF from the Stepan Company
[11] Zinc Pyrithione, supplier Lonza
[12] Selenium disulfide, supplier Eskay
[12] Cetyl Alcohol, supplier P&G
13 Stearyl Alcohol, supplier P&G
[14] Methocel, supplier Dow Chemical

| Ingredient | 10 | 11 | 12 |
|---|---|---|---|
| | | Wt % | |
| Ammonium Laureth Sulfate[1] | 14.1 | 14.1 | 14.1 |
| Ammonium Lauryl Sulfate[2] | 3.1 | 3.1 | 3.1 |
| Ammonium Xylenesulfonate[3] | 0.45 | 0.45 | 0.45 |
| TWEEN 60[4] | 3.0 | 3.0 | 3.0 |
| Polyquaternium-10[5] | 0.35 | 0.35 | 0.35 |
| Cetrimonium Chloride[6] | 0.5 | 0.5 | 0.5 |
| Sulfur[7] | 2.0 | 2.0 | 2.0 |
| Dimethicone[8] | 0.60 | 0.60 | 0.60 |
| Ethylene Glycol Distearate[9] | 3.0 | 3.0 | 3.0 |
| Cocamide MEA[10] | 3.0 | 3.0 | 3.0 |
| Selenium Sulfide[11] | 0.5 | 0.25 | 0.1 |
| Neat Fragrance | 0.65 | 0.85 | 1.0 |
| Malodor reducing composition | 0.175 | 0.175 | 0.175 |
| Cetyl Alcohol[12] | 0.42 | 0.42 | 0.42 |
| DMDM Hydantoin | 0.40 | 0.40 | 0.40 |
| Sodium Chloride | 0.30 | 0.30 | 0.30 |
| Stearyl Alcohol[13] | 0.20 | 0.20 | 0.20 |
| Hydroxypropyl Methylcellulose[14] | 0.02 | 0.02 | 0.02 |
| Water | Q.S. | Q.S. | Q.S. |

[1] Ammonium Laureth Sulfate at 25% active, supplier: P&G
[2] Ammonium Lauryl Sulfate at 25% active, supplier: P&G
[3] Ammonium Xylene Sulfonate 40% active, supplier: Stepan
[4] Polysorbate 60, upplier: Croda
[5] UCARE Polymer LR400, supplier- Dow Chemical
[6] cetrimonium chloride, supplier - Croda
[7] Sulfur USP, supplier Universal Preserv-A-Chem
[8] Viscasil 330M from Momentive Performance Materials with a viscosity of 330,000 cSt (centistokes).
[9] Ethylene Glycol Disterate, supplier: Stepan
[10] Ninol COMF from the Stepan Company
[11] Zinc Pyrithione, supplier Lonza
[12] Selenium disulfide, supplier Eskay
[12] Cetyl Alcohol, supplier P&G
[13] Stearyl Alcohol, supplier P&G
[14] Methocel, supplier Dow Chemical

| Ingredients | 13 | 14 | 15 |
|---|---|---|---|
| | | Wt % | |
| Sodium Laureth Sulfate[1] | 14.1 | 11.5 | 11.5 |
| Sodium Lauryl Sulfate [2] | 3.1 | 1.5 | 1.5 |
| Sodium Xylenesulfonate[3] | 0.50 | 3.0 | 3.0 |
| Cocamidopropyl Betaine[4] | — | 1.3 | 1.3 |
| Guar Hyrdroxypropyltrimonium chloride[5] | — | 0.3 | 0.3 |
| PQ-76[6] | — | 0.03 | — |
| Acrylamide/trimethylammoniopropylmethacrylamide[7] | — | — | 0.01 |
| Selenium Sulfide[8] | 1.0 | 1.0 | 0.2 |
| Sulfur[9] | — | — | — |
| Dimethicone[10] | 0.60 | 0.8 | 2.7 |
| Ethylene Glycol Distearate[11] | 3.0 | 1.5 | 1.5 |
| Cocamide MEA[12] | 3.0 | 2.0 | 2.0 |
| Zinc Pyrithione[13] | — | — | 1.0 |
| Zinc Carbonate[14] | — | — | 1.61 |
| Fragrance | 0.65 | 0.85 | 1.0 |
| Malodor reducing composition | 0.15 | 0.175 | 0.1 |
| Cetyl Alcohol[15] | 0.42 | 0.04 | 0.04 |
| Stearyl Alcohol[16] | 0.20 | 0.08 | 0.08 |
| DMDM Hydantoin | 0.40 | — | — |
| Methylchloroisothiazolinone and Methylisothiazolinone | 0.5 | 0.005 | 0.005 |
| Sodium Chloride | 0.30 | — | — |
| Hydroxypropyl Methylcellulose[17] | 0.02 | 0.02 | 0.02 |
| Water | Q.S. | Q.S. | Q.S. |

[1]Sodium Laureth Sulfate at 28% active, supplier: P&G
[2] Sodium Lauryl Sulfate at 29% active, supplier: P&G
[3]Sodium Xylene Sulfonate 40% active, supplier: Stepan
[4]Amphosol HCA from the Stepan Company
[5]Jaguar C500 from Rhodia; mw 500,000 cd 0.8 meq/g
[6]PQ-76 from Rhodia; mw 100,000 cd 1.6 meq/g
[7]AM/APTAC mw 1,100,000 cd 1.8 meq/g, supplier ASI Specialty Ingredients
[8]Selenium disulfide, supplier Eskay
[9]Sulfur USP, supplier Universal Preserv-A-Chem
[10]Viscasil 330M from Momentive Performance Materials with a viscosity of 330,000 cSt (centistokes).
[11]Ethylene Glycol Disterate, supplier: Stepan
[12]Ninol COMF from the Stepan Company
[13]Zinc Pyrithione, supplier Lonza
[14]Zinc Carbonate Basic, supplier Pan Continental Chemical
[15]Cetyl Alcohol, supplier P&G
[16]Stearyl Alcohol, supplier P&G
[17]Methocel, supplier Dow Chemical

| Ingredients | 16 | 17 | 18 |
|---|---|---|---|
| | | Wt % | |
| Sodium Laureth Sulfate[1] | 11.5 | 11.5 | 11.5 |
| Sodium Lauryl Sulfate [2] | 1.5 | 1.5 | 1.5 |
| Sodium Xylenesulfonate[3] | 3.0 | 3.0 | 3.0 |
| Cocamidopropyl Betaine[4] | 1.3 | 1.3 | 1.3 |
| Guar Hyrdroxypropyltrimonium chloride[5] | 0.3 | 0.3 | 0.3 |
| PQ-76[6] | 0.03 | 0.03 | — |
| Acrylamide/trimethylammoniopropylmethacrylamide[7] | — | — | 0.01 |
| Selenium Sulfide[8] | 1.0 | — | 0.1 |
| Sulfur[9] | 2.0 | 5.0 | 2.0 |
| Dimethicone[10] | 0.8 | 0.8 | 2.7 |
| Ethylene Glycol Distearate[11] | 1.5 | 1.5 | 1.5 |
| Cocamide MEA[12] | 2.0 | 2.0 | 2.0 |
| Zinc Pyrithione[13] | — | — | — |
| Zinc Carbonate[14] | — | — | — |
| Fragrance | 0.85 | 0.85 | 1.0 |
| Malodor reducing composition | 0.175 | 0.175 | 0.1 |
| Cetyl Alcohol[15] | 0.04 | 0.04 | 0.04 |
| Stearyl Alcohol[16] | 0.08 | 0.08 | 0.08 |
| DMDM Hydantoin | — | — | — |
| Methylchloroisothiazolinone and Methylisothiazolinone | 0.005 | 0.005 | 0.005 |
| Sodium Chloride | — | — | — |
| Hydroxypropyl Methylcellulose[17] | 0.02 | 0.02 | 0.02 |
| Water | Q.S. | Q.S. | Q.S. |

[1]Sodium Laureth Sulfate at 28% active, supplier: P&G
[2] Sodium Lauryl Sulfate at 29% active, supplier: P&G
[3]Sodium Xylene Sulfonate 40% active, supplier: Stepan
[4]Amphosol HCA from the Stepan Company
[5]Jaguar C500 from Rhodia; mw 500,000 cd 0.8 meq/g
[6]PQ-76 from Rhodia; mw 100,000 cd 1.6 meq/g
[7]AM/APTAC mw 1,100,000 cd 1.8 meq/g, supplier ASI Specialty Ingredients
[8]Selenium disulfide, supplier Eskay
[9]Sulfur USP, supplier Universal Preserv-A-Chem
[10]Viscasil 330M from Momentive Performance Materials with a viscosity of 330,000 cSt (centistokes).
[11]Ethylene Glycol Disterate, supplier: Stepan
[12]Ninol COMF from the Stepan Company
[13]Zinc Pyrithione, supplier Lonza
[14]Zinc Carbonate Basic, supplier Pan Continental Chemical
[15]Cetyl Alcohol, supplier P&G
[16]Stearyl Alcohol, supplier P&G
[17]Methocel, supplier Dow Chemical Rinse Out Conditioner Examples The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

| Components | Ex. 1 | Ex. 2 | Ex. 3 | Ex. 4 | Ex. 5 |
|---|---|---|---|---|---|
| Polyquaternium-6 *1 | 0.075 | — | — | — | — |
| Polyquaternium-6 *2 | — | 0.075 | 0.075 | 0.075 | 0.075 |
| Zinc pyrithione *3 | 0.5 | 0.75 | 0.75 | 0.75 | 0.75 |
| Zinc carbonate *4 | 1.6 | 1.6 | 1.6 | — | 1.6 |
| Selenium Disulfide *5 | 1.0 | 0.5 | 1.0 | 1.0 | 1.0 |
| Sulfur *6 | — | — | — | — | — |
| Stearamidopropyldimethylamine | 2.0 | — | — | — | — |
| 1-glutamic acid | 0.64 | — | — | — | — |
| Behenyl trimethyl ammonium methosulfate | — | 1.8 | 1.8 | 1.8 | 1.8 |
| Dicetyl dimethyl ammonium chloride | — | 0.52 | 0.52 | 0.52 | 0.52 |
| Cetyl alcohol | 2.5 | 1.1 | 1.1 | 1.1 | 1.1 |
| Stearyl alcohol | 4.5 | 2.75 | 2.75 | 2.75 | 2.75 |
| Polydimethylsiloxane *7 | 0.6 | — | — | — | — |
| Aminosilicone *8 | — | 0.75 | 0.75 | 0.75 | 0.75 |
| Preservatives | 0.45 | 0.4 | 0.4 | 0.4 | 0.4 |
| Perfume | 0.5 | 0.5 | 0.5 | 0.5 | 0.5 |
| Malodor Reducing Composition | 0.125 | 0.1 | 0.25 | 0.175 | — |
| Deionized Water | q.s. to 100% | | | | |
| Method of preparation | I | II | I | II | I |

*1 Polyquaternium-6: Poly(diallyldimethylammonium chloride) supplied with a tradename Merquat 100 from Lubrizol, having a charge density of about 6.2 meq/g, and molecular weight of about 150,000 g/mol
*2 Polyquaternium-6: Poly(diallyldimethylammonium chloride) supplied with a tradename Merquat 106 from Lubrizol having a charge density of about 6.2 meq/g, and molecular weight of about 15,000 g/mol
*3 Zinc pyrithione: having a particle size of from about 1 to about 10 microns
*4 Zinc carbonate: having a particle size of from about 1 to about 10 microns
*5 Selenium Disulfide, from Eskay
*6 Sulfur, from Universal Preserv-A-Chem
*7 Polydimethylsiloxane: having a viscosity of 10,000 cSt
*8 Aminosilicone: Terminal aminosilicone which is available from GE having a viscosity of about 10,000 mPa · s, and having following formula:
$(R_1)_a G_{3-a}$—Si—$(-OSiG_2)_n$—O—$SiG_{3-a}(R_1)_a$ wherein G is methyl; a is an integer of 1; n is a number from 400 to about 600; $R_1$ is a monovalent radical conforming to the general formula $C_q H_{2q} L$, wherein q is an integer of 3 and L is —$NH_2$.

| Components | Ex. 6 | Ex. 7 | Ex. 8 |
|---|---|---|---|
| Polyquaternium-6 *1 | — | — | — |
| Polyquaternium-6 *2 | 0.075 | 0.075 | 0.075 |
| Zinc pyrithione *3 | 0.75 | 0.75 | 0.75 |
| Zinc carbonate *4 | 1.6 | 1.6 | 1.6 |
| Selenium Disulfide *5 | 1.0 | 0.1 | — |
| Sulfur *6 | 3.5 | 2.0 | 2.0 |
| Stearamidopropyldimethylamine | — | — | — |
| 1-glutamic acid | — | — | — |
| Behenyl trimethyl ammonium methosulfate | 1.8 | 1.8 | 1.8 |
| Dicetyl dimethyl ammonium chloride | 0.52 | 0.52 | 0.52 |
| Cetyl alcohol | 1.1 | 1.1 | 1.1 |
| Stearyl alcohol | 2.75 | 2.75 | 2.75 |
| Polydimethylsiloxane *7 | — | — | — |
| Aminosilicone *8 | 0.75 | 0.75 | 0.75 |
| Preservatives | 0.4 | 0.4 | 0.4 |
| Perfume | 0.5 | 0.5 | 0.5 |
| Malodor Reducing Composition | 0.175 | 0.25 | 0.25 |
| Deionized Water | QS to 100% | | |
| Method of preparation | II | II | II |

*1 Polyquaternium-6: Poly(diallyldimethylammonium chloride) supplied with a tradename Merquat 100 from Lubrizol, having a charge density of about 6.2 meq/g, and molecular weight of about 150,000 g/mol
*2 Polyquaternium-6: Poly(diallyldimethylammonium chloride) supplied with a tradename Merquat 106 from Lubrizol having a charge density of about 6.2 meq/g, and molecular weight of about 15,000 g/mol
*3 Zinc pyrithione: having a particle size of from about 1 to about 10 microns
*4 Zinc carbonate: having a particle size of from about 1 to about 10 microns
*5 Selenium Disulfide, from Eskay
*6 Sulfur, from Universal Preserv-A-Chem
*7 Polydimethylsiloxane: having a viscosity of 10,000 cSt
*8 Aminosilicone: Terminal aminosilicone which is available from GE having a viscosity of about 10,000 mPa · s, and having following formula:
$(R_1)_a G_{3-a}$—Si—(—O$SiG_2$)$_n$—O—$SiG_{3-a}(R_1)_a$ wherein G is methyl; a is an integer of 1; n is a number from 400 to about 600; $R_1$ is a monovalent radical conforming to the general formula $C_qH_{2q}L$, wherein q is an integer of 3 and L is —$NH_2$.

Method of Preparation

The conditioning compositions of "Ex. 1" through "Ex.3" and "CEx. i as shown above can be prepared by any conventional method well known in the art. They are suitably made by one of the following Methods I or II as shown above.

Method I

Cationic surfactants and high melting point fatty compounds are added to water with agitation, and heated to about 80° C. The mixture is cooled down to about 55° C. and gel matrix is formed. Zinc carbonates, and if included, silicones and preservatives, are added to the gel matrix with agitation. Then, zinc pyrithione, and if included, polymers are added with agitation at about 45° C. Then, if included, other components such as perfumes are added with agitation. Then the composition is cooled down to room temperature.

Method II

Cationic surfactants and high melting point fatty compounds are mixed and heated to from about 66° C. to about 85° C. to form an oil phase. Separately, water is heated to from about 20° C. to about 48° C. to form an aqueous phase. In Becomix® direct injection rotor-stator homogenizer, the oil phase is injected and it takes 0.2 second or less for the oils phase to reach to a high shear field having an energy density of from $1.0 \times 10^5$ J/m$^3$ to $1.0 \times 10^7$ J/m$^3$ where the aqueous phase is already present. A gel matrix is formed at a temperature of above 50° C. to about 60° C. Silicones, Perfume, Polymer and Preservative, if included, are added to the gel matrix with agitation at temperature below 55° C. and mixed well. Then, zinc carbonate, if included, followed by zinc pyrithione, are added to the gel matrix with agitation at temperature below 50° C. and mix well. Finally the composition is cooled down to room temperature.

Leave on Treatment Formulations and Examples

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Leave on Treatment Examples

| | Examples | | | | | |
|---|---|---|---|---|---|---|
| | 1 Active wt % | 2 Active wt % | 3 Active wt % | 4 Active wt % | 5 Active wt % | 6 Active wt % |
| Water | Q.S. | Q.S. | Q.S. | Q.S. | Q.S. | Q.S. |
| Alcohol 100% (Ethanol) | 50 | 0 | 50 | 0 | 50 | 0 |
| Isoproryl Alcohol | 0 | 0 | 0 | 0 | 0 | 0 |
| Acrylates/C10-30 alkyl acrylate crosspolymer *1 | 0.35 | 0.2 | 0.35 | 0.2 | 0.35 | 0.2 |
| Zinc pyrithione *2 | 0.1 | 0.07 | — | — | — | — |
| Selenium Sulfide *3 | 0.1 | 0.1 | — | — | 0.1 | 0.1 |
| Sulfur *4 | — | — | 2.0 | 2.0 | 2.0 | 2.0 |
| Panthenol | 0.15 | 0 | 0.15 | 0 | 0.15 | 0 |
| Niacinamide | 2.5 | 0 | 2.5 | 0 | 2.5 | 0 |
| Caffeine | 0.75 | 0 | 0.75 | 0 | 0.75 | 0 |
| Glycerin | 0.5 | 0 | 0.5 | 0 | 0.5 | 0 |
| Propylene Glycol | 0 | 1 | 0 | 1 | 0 | 1 |
| Menthol | 0 | 0.5 | 0 | 0.5 | 0 | 0.5 |
| Tapicoa Starch Polymethylsilsesuioxane *5 | 0 | 1 | 0 | 1 | 0 | 1 |
| Benzyl Alcohol | 0.12 | 0.5 | 0.12 | 0.5 | 0.12 | 0.5 |
| Methylisothiazolinone *6 | 0 | 0.05 | 0 | 0.05 | 0 | 0.05 |

-continued

|  | Examples | | | | | |
| --- | --- | --- | --- | --- | --- | --- |
|  | 1 Active wt % | 2 Active wt % | 3 Active wt % | 4 Active wt % | 5 Active wt % | 6 Active wt % |
| PEG-40 Hydrogenated Castor Oil *7 | 0 | 0.5 | 0 | 0.5 | 0 | 0.5 |
| Tetrahydroxypropyl Ethylenediamine *8 | 0.12 | 0.14 | 0.12 | 0.14 | 0.12 | 0.14 |
| Fragrance | 0.4 | 0.2 | 0.4 | 0.2 | 0.4 | 0.2 |
| Malodor Reducing Composition | 0.15 | 0.1 | 0.15 | 0.1 | 0.15 | 0.1 |

*1 as in Carbopol Ultrez 21 available from Lubrizol
*2 as in ZPT from Lonza Personal Care
*3 as in selenium sulfide from Eskay
*4 as in Sulfur, from Universal Preserv-A-Chem
*5 as in Neolone 950 from Rohm and Haas
*6 as in Cremophor RH-40 Surfactant from BASF
*7 as in Neutrol Te from BASF
*8 as in Trolamine from Dow Chemical In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition Examples/Combinations A. A hair care composition comprising, based on total composition weight,
  a) a sum total of from about 0.0001% to about 2% of alpha,alpha,6,6-tetramethyl bicyclo[3.1.1]hept-2-ene-propanal) and one or more malodor reduction materials having a Sulfur MORV>3;
  b) from about 0.01% to about 10% of a scalp active material selected from the group consisting of selenium sulfide, sulfur and mixtures thereof;
  c) from about 0.1% to about 40%, of a surfactant.
B. The composition according to Paragraph A, wherein the malodor reduction materials are selected from the group consisting of 2'-isopropyl-1,7,7-trimethylspiro[bicyclo[2.2.1]heptane-2,4'-[1,3]dioxane], 1',1',5',5'-tetramethyl-hexahydro-2'H,5'H-spiro[[1,3]dioxolane-2,8'-[2,4a]methanonaphthalene, 3a,4,5,6,7,7a-hexahydro-1H-4,7-methanoinden-6-yl acetate, 3a,4,5,6,7,7a-hexahydro-1H-4,7-methanoinden-6-yl acetate, (3R,3aR,6S,7S,8aS)-6-methoxy-3,6,8,8-tetramethyloctahydro-1H-3a,7-methanoazulene, Ethyl (1R,2R,3R,4R)-3-isopropylbicyclo[2.2.1]hept-5-ene-2-carboxylate), (3aR,5aR,9aR,9bR)-3a,6,6,9a-tetramethyldodecahydronaphtho[2,1-b]furan), alpha,alpha,6,6-tetramethylbicyclo[3.1.1]hept-2-ene-propanal, 4,5-epoxy-4,11,11-trimethyl-8-methylenebicyclo(7.2.0)undecane), (4aR,8aS)-7-methyloctahydro-1,4-methanonaphthalen-6(2H)-one), (5-methoxyoctahydro-1H-4,7-methanoindene-2-carbaldehyde), (2R,4a'R,8a'R)-3,7'-dimethyl-3',4',4a',5',8',8a'-hexahydro-1'H-spiro[oxirane-2,2'-[1,4]methanonaphthalene]), 2,2,6,6,7,8,8-heptamethyldecahydro-2H-indeno[4,5-b]furan, 1,3,4,6,7,8alpha-hexahydro-1,1,5,5-tetramethyl-2H-2,4alpha-methanophtalen-8(5H)-one, (3a,4,5,6,7,7a-hexahydro-1H-4,7-methanoinden-5-yl isobutyrate), (3S,5aR,7aS,11 aS, 11 bR)-3,8,8,11a-tetramethyldodecahydro-5H-3,5a-epoxynaphtho[2,1-c]oxepine), 8,8-dimethyl-3a,4,5,6,7,7a-hexahydro-1H-4,7-methanoinden-6-yl propionate, (4aR,5R,7aS,9R)-2,2,5,8,8,9a-hexamethyloctahydro-4H-4a,9-methanoazuleno[5,6-d][1 1,3]dioxole), 2-(8-isopropyl-6-methylbicyclo[2.2.2]oct-5-en-2-yl)-1,3-dioxolane), 3a,4,5,6,7,7a-hexahydro-1H-4,7-methanoinden-6-yl pivalate, (3a,5,6,7,8,8b-hexahydro-2,2,6,6,7,8,8-heptamethyl-4H-indeno(4,5-d)-1,3-dioxole), (3R,3aS,6R,7R,8aS)-3,6,8,8-tetramethyloctahydro-1H-3a,7-methanoazulen-3-yl formate (3R,3aS,6R,7R,8aS)-3,6,8,8-tetramethyloctahydro-1H-3a, 7-methanoazulen-6-ol, (1-((2S,3S)-2,3,8,8-tetramethyl-1,2,3,4,5,6,7,8-octahydronaphthalen-2-yl)ethan-1-one), ((E)-4-((3aS,7aS)-octahydro-5H-4,7-methanoinden-5-ylidene)butanal), (Z)-4,11,11-trimethyl-8-methylenebicyclo[7.2.0]undec-3-en-5-yl acetate, (1aR,4S,4aS,7R,7aS,7bS)-1,1,4,7-tetramethyldecahydro-1H-cyclopropa[e]azulen-4-ol), ((Z)-6-ethylideneoctahydro-2H-5,8-methanochromen-2-one), 1-((3R,3aR,7R,8aS)-3,6,8,8-tetramethyl-2,3,4,7,8,8a-hexahydro-1H-3a,7-methanoazulen-5-yl)ethan-1-one), 3,5,5,6,7,8,8-heptamethyl-5,6,7,8-tetrahydronaphthalene-2-carbonitrile, 2-(cyclohexyloxy)-1,7,7-trimethylbicyclo[2.2.1]heptane (E)-4-((3aR,4R,7R,7aR)-1,3a,4,6,7,7a-hexahydro-5H-4,7-methanoinden-5-ylidene)-3-methylbutan-2-ol), ((E)-3,7-dimethylocta-2,6-dien-1-yl palmitate) and mixtures thereof.
C. The composition according to paragraph according to A-B, wherein malodor reduction material has a C log P>3.
D. The composition according to paragraph according to A-C, wherein the malodor reduction material has a VP>0.005.
E. The composition according to paragraph A-D, wherein the malodor reduction material has a MORV>3, a C log P>3 and a VP>0.005.
F. The composition according to paragraph A-E, wherein the malodor reduction material is selected from the group consisting of 2'-isopropyl-1,7,7-trimethylspiro[bicyclo[2.2.1]heptane-2,4'-[1,3]dioxane, 1',1',5',5'-tetramethylhexahydro-2'H,5'H-spiro[[1,3]dioxolane-2,8'-[2,4a]methanonaphthalene] K, SPIRO[FURAN-2(3H),5'-(4,7-METHANO-5H-INDENE], DECAHYDRO, (3R,3aR,6S,7S,8aS)-6-methoxy-3,6,8,8-tetramethyloctahydro-1H-3a,7-methanoazulene, Ethyl (1R,2R,3R,4R)-3-isopropylbicyclo[2.2.1]hept-5-ene-2-carboxylate, 3aR,5aR,9aR,9bR)-3a,6,6,9a-tetramethyldodecahydronaphtho[2,1-b]furan, alpha, alpha,6,6-tetramethylbicyclo[3.1.1]hept-2-ene-propanal, 4,5-epoxy-4,11,1-trimethyl-8-methylenebicyclo(7.2.0)undecane, 2'-isopropyl-1,7,7-trimethylspiro[bicyclo[2.2.1]heptane-2,4'-[1,3]dioxane and mixtures thereof.

G. The composition according to paragraph A-F, wherein the surfactant is selected from the group consisting of anionic, amphoteric or zwitterionic, cationic or mixtures thereof.

H. The composition according to paragraph A-G, wherein the composition comprises the sum total of from about 0.001% to about 0.75% of the malodor reduction material.

I. The composition according to paragraph A-H, wherein the composition comprises the sum total of from about 0.01% to about 0.5% of the malodor reduction material.

J. The composition according to paragraph A-I, wherein the composition comprising one or more perfume raw materials.

K. The composition according to paragraph A-J, wherein a method of controlling malodors comprising: contacting a situs comprising a malodor and/or a situs that will become malodorous with a hair care composition selected from the group consisting of the hair care composition of paragraph A-J.

L. The composition according to A-K, wherein said situs is a head of hair and said contacting step comprises contacting said head of hair with a sufficient amount of a hair care composition to provide said hair with a level of malodor reduction material at least 0.0001 mg of malodor reduction material per head of hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. A hair care composition comprising, based on total composition weight,
   a) a sum total of from about 0.0001% to about 2% of a malodor reduction material consisting of alpha,alpha,6,6-tetramethylbicyclo[3.1.1]hept-2-ene-propanal) and malodor reduction materials 2'-isopropyl-1,7,7-trimethylspiro[bicyclo[2.2.1]heptane-2,4'-[1,3]dioxane, 1',1',5',5'-tetramethylhexahydro-2'H,5'H-spiro[[1,3]dioxolane-2,8'-[2,4a]methanonaphthalene] K, SPIRO [FURAN-2(3H),5'-(4,7-METHANO-5H-INDENE], DECAHYDRO, (3R,3aR,6S,7S,8aS)-6-methoxy-3,6,8,8-tetramethyloctahydro-1H-3a,7-methanoazulene, Ethyl (1R,2R,3R,4R)-3-isopropylbicyclo[2.2.1]hept-5-ene-2-carboxylate, (3aR,5aR,9aR,9bR)-3a,6,6,9a-tetramethyldodecahydronaphtho[2,1-b]furan, bicyclo[3.1.1]hept-2-ene-propanal, 4,5-epoxy-4,11,11-trimethyl-8-methylenebicyclo(7.2.0)undecane, and 2'-isopropyl-1,7,7-trimethylspiro[bicyclo[2.2.1]heptane-2,4'-[1,3]dioxane;
   b) from about 0.01% to about 10% of a scalp active material wherein the scalp active material is coal tar;
   c) from about 0.1% to about 40%, of an anionic surfactant.

2. A hair care composition according to claim 1 wherein the composition comprises the sum total of from about 0.001% to about 0.75% of the malodor reduction material.

3. A hair care composition according to claim 1 wherein the composition comprises the sum total of from about 0.01% to about 0.5% of the malodor reduction material.

4. A hair care composition according claim 1, the composition comprising one or more perfume raw materials.

5. A method of controlling malodors comprising: contacting a situs comprising a malodor and/or a situs that will become malodorous with the hair care composition of claim 1.

6. The method of claim 5 wherein, said situs is a head of hair and said contacting step comprises contacting said head of hair with a sufficient amount of the hair care composition to provide said hair with a level of malodor reduction material at least 0.0001 mg of malodor reduction material per head of hair.

* * * * *